United States Patent
Deliencourt-Godefroy et al.

(10) Patent No.: US 10,640,441 B2
(45) Date of Patent: May 5, 2020

(54) DIFLUORINATED COMPOUNDS AS DEPIGMENTING OR LIGHTENING AGENTS

(71) Applicant: TFCHEM, Val de Reuil (FR)

(72) Inventors: Geraldine Deliencourt-Godefroy, Bois D'Ennebourg (FR); Lenaig Lopes, Le Petit Quevilly (FR)

(73) Assignee: TFCHEM, Val-de-Reuil (FR)

( * ) Notice: Subject to any disclaimer, the term of this patent is extended or adjusted under 35 U.S.C. 154(b) by 0 days.

(21) Appl. No.: 16/327,776

(22) PCT Filed: Aug. 24, 2017

(86) PCT No.: PCT/EP2017/071350
§ 371 (c)(1),
(2) Date: Feb. 22, 2019

(87) PCT Pub. No.: WO2018/037086
PCT Pub. Date: Mar. 1, 2018

(65) Prior Publication Data
US 2019/0322608 A1 Oct. 24, 2019

(30) Foreign Application Priority Data

Aug. 24, 2016 (WO) .................. PCT/IB2016/001354

(51) Int. Cl.
| | |
|---|---|
| *C07C 43/253* | (2006.01) |
| *A61K 8/69* | (2006.01) |
| *C07C 43/247* | (2006.01) |
| *C07C 217/52* | (2006.01) |
| *C07C 217/74* | (2006.01) |
| *A61Q 19/02* | (2006.01) |
| *C07C 41/22* | (2006.01) |
| *C07C 213/06* | (2006.01) |

(52) U.S. Cl.
CPC .............. *C07C 43/253* (2013.01); *A61K 8/69* (2013.01); *C07C 43/247* (2013.01); *C07C 217/52* (2013.01); *C07C 217/74* (2013.01); *A61Q 19/02* (2013.01); *C07C 41/22* (2013.01); *C07C 213/06* (2013.01); *C07C 2601/14* (2017.05)

(58) Field of Classification Search
CPC combination set(s) only.
See application file for complete search history.

(56) References Cited

FOREIGN PATENT DOCUMENTS

| | | | |
|---|---|---|---|
| WO | WO 2012/160218 A1 | 11/2012 | |
| WO | WO-2012160218 A1 * | 11/2012 | ............. C07C 43/29 |
| WO | WO 2013/103874 A1 | 7/2013 | |

OTHER PUBLICATIONS

Boissy et al., "Deoxy Arbutin: A Novel Reversible Tyrosinate Inhibitor With Effective in Vivo Skin Lightening Potency", Experimental Dermatology, vol. 14, Jan. 1, 2005, pp. 601-608.
International Search Report issued in PCT/EP2017/071350, dated Oct. 30, 2017.
Written Opinion of the International Searching Authority issued in PCT/EP2017/071350, dated Oct. 30, 2017.
Chao-Hsun Yang, et al., "Comparative Study on the Photostability of Arbutin and Deoxy Arbutin: Sensitivity to Ultraviolet Radiation and Enhanced Photostability by the Water-Soluble Sunscreen, Benzophenone-4", Biosci. Biotechnol. Biochem., 2013, vol. 77, No. 5, pp. 1127-1130.
Flemming Gundorph Hansen, et al., "A Short Synthesis of (+)— Cyclophellitol", J. Org. Chem, 2005, vol. 70, pp. 10139-10142.
Garehatty Rudrappa Kanthraj, "Skin-lightening agents: New chemical and plant extracts—ongoing search for the Holy Grail!", Indian J Dermatol Venereol Leprol, Jan.-Feb. 2010, vol. 76, Issue 1, pp. 3-6.
Jody P. Ebanks et al., "Mechanisms Regulating Skin Pigmentation: The Rise and Fall of Complexion Coloration", International Journal of Molecular Sciences, 2009, vol. 10, pp. 4066-4087, ISSN: 1422-0067, DOI: 10.3390/ijms10094066.

* cited by examiner

*Primary Examiner* — Andrew S Rosenthal
(74) *Attorney, Agent, or Firm* — Sunit Talapatra; Foley & Lardner LLP

(57) ABSTRACT

The present invention relates to a compound having the following formula (I) as well as a method for preparing such a compound, a cosmetic or pharmaceutical composition containing such a compound, and the use thereof as a depigmenting, lightening, bleaching or whitening agent and for treating pigmentation disorders, notably by topical application on the skin.

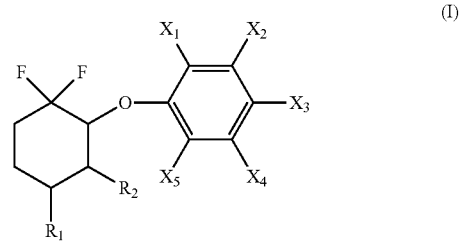

(I)

22 Claims, 1 Drawing Sheet

DIFLUORINATED COMPOUNDS AS DEPIGMENTING OR LIGHTENING AGENTS

CROSS-REFERENCE TO RELATED APPLICATIONS

Figure 1:
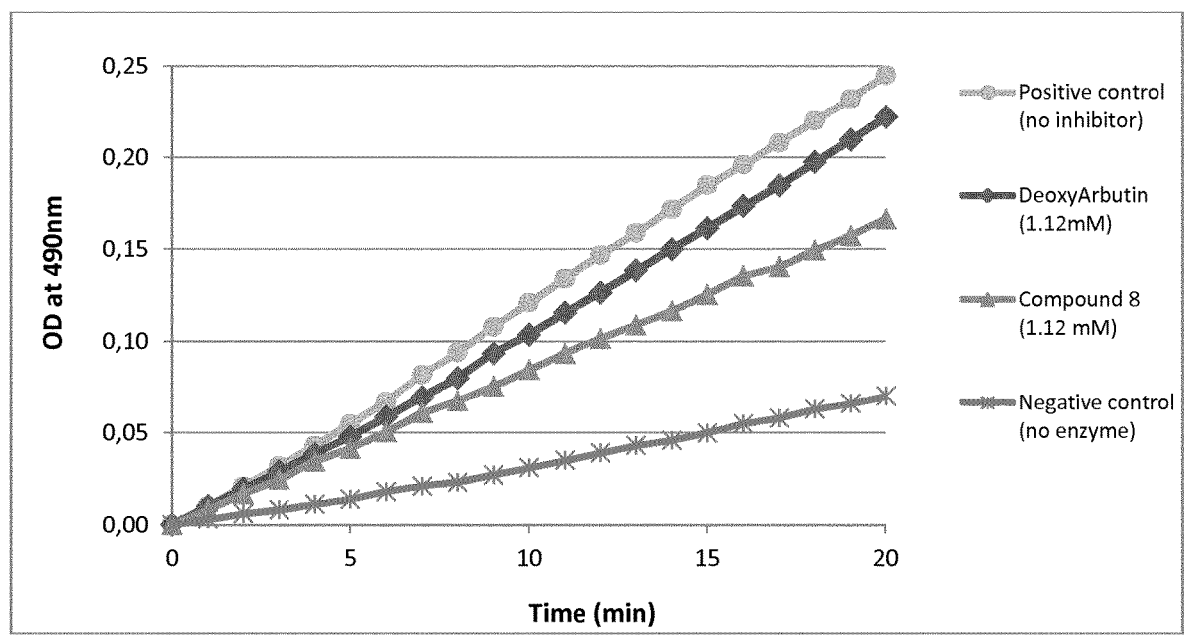

This application is the National Phase of International Patent Application No. PCT/EP2017/071350, filed Aug. 24, 2017, published on Mar. 1, 2018 as WO/2018/037086 A1, which claims priority to International Patent Application No. PCT/IB2016/001354, filed Aug. 24, 2016. The contents of these applications are herein incorporated by reference in their entirety.

The invention described herein relates to novel difluorinated compounds, their use for cosmetic and pharmaceutical applications and their preparation processes. Such compounds can particularly be used as depigmenting, lightening, bleaching or whitening agents, as well as for the treatment of disturbed pigmentation.

The need for efficacious and safe skin lightening products led to a number of skin lightening agents being developed such as kojic acid, glycolic acid, azelaic acid, catechins, hydroquinone, arbutin, and more recently deoxy arbutin. They have been developed for lightening skin or treating pigmentation disorders. These compounds act as inhibitors of tyrosinase which catalyze the formation of melanin pigment that gives skin and hair color. A too important production of melanin, resulting for example of a prolonged sun exposure, hormone changes, or medical treatment, can create an hyperpigmentation of skin (*Int. J. Mol. Sci.* 2009, 10, 4066-4087).

Tyrosinase inhibitors have become important in cosmetic products in the treatment of hyperpigmentation.

Derivatives of hydroquinone, such as arbutin (a glycosylated form of hydroquinone), deoxyarbutin (a synthetic form of arbutin without the hydroxyl moieties) or derivatives thereof (described for example in WO 2013/103874) are very attractive compounds.

However, the cleavage of acetal functional group leads to the release of hydroquinone, which is limited in cosmetic applications due to possible side effects (*Biosci. Biotechnol. Biochem.* 2013, 77, 1127-1130; *Indian J. Dermatol. Venereol. Leprol.* 2010, 76, 3-6). More stable derivatives of hydroquinone (WO 2012/160218) have been developed, however such compounds like arbutin suffer of a poor skin permeation to the target site of action, i.e. the melanocytes. That's why the development of new depigmenting or lightening agents more efficient and safer than those already presented remains an important target.

It has been surprisingly discovered that new difluorinated derivatives with hydroxyl and/or amino group(s) present(s) on different positions of the carbocyclic moiety have improved efficacy, safety and permeation but also are accessible with a shorter chemical synthesis process allowing reducing their cost of production.

The present invention relates thus to a compound having the following formula I:

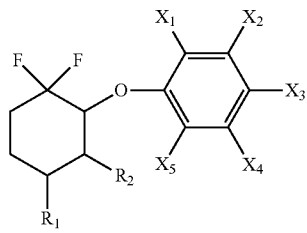

or a cosmetically or pharmaceutically acceptable salt thereof, a stereoisomer or a mixture of stereoisomers in any proportion, particularly an enantiomer or a mixture of enantiomers, and more particularly a racemate mixture, wherein:

$R_1$ represents a hydrogen atom, OH, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$, $R_2$ represents OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, $OSO_3R_{22}$, $NH_2$, $NHR_{33}$, or $NR_{33}R_{34}$, $X_1$, $X_2$, $X_3$, $X_4$ and $X_5$ represent, independently from one another, a hydrogen atom, OH, $OSiR_{23}R_{24}R_{25}$, $OR_{26}$, $OC(O)R_{27}$, $OCO_2R_{28}$, $OC(O)NR_{29}R_{30}$, $OP(O)(OR_{31})_2$, or $OSO_3R_{32}$, with:

$R_3$, $R_4$, $R_5$, $R_{13}$, $R_{14}$, $R_{15}$, $R_{23}$, $R_{24}$ and $R_{25}$ representing, independently from one another, a $(C_1-C_6)$alkyl, aryl, aryl-$(C_1-C_6)$alkyl or $(C_1-C_6)$alkyl-aryl group, $R_6$, $R_{16}$ and $R_{26}$ representing, independently from one another, a O-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_7$, $R_8$, $R_{17}$, $R_{18}$, $R_{27}$ and $R_{28}$ representing, independently from one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_9$, $R_{10}$, $R_{19}$, $R_{20}$, $R_{29}$ and $R_{30}$ representing, independently from one another, a hydrogen atom; a N-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_{11}$, $R_{12}$, $R_{21}$, $R_{22}$, $R_{31}$ and $R_{32}$ representing, independently from one another, a hydrogen atom or a $(C_1-C_6)$alkyl group, and $R_{33}$ and $R_{34}$ representing, independently from one another, a N-protecting group; or a $(C_1-C_6)$alkyl, $(C_2-$ $C_6$)alkenyl, ($C_2$-$C_6$)alkynyl, ($C_3$-$C_7$)cycloalkyl, 5- to 7-membered heterocycloalkyl, aryl, heteroaryl, aryl-($C_1$-$C_6$)alkyl, heteroaryl-($C_1$-$C_6$)alkyl, ($C_1$-$C_6$)-alkyl-aryl or ($C_1$-$C_6$)-alkyl-heteroaryl group, said group being optionally substituted by one or several groups selected from a halogen atom, OH, COOH and CHO.

As used in the present invention:

"cosmetically or a pharmaceutically acceptable" concerns what is useful for the preparation of a cosmetic or pharmaceutical composition, which is generally non-toxic, safe and acceptable for pharmaceutical and cosmetic use.

a "cosmetically or pharmaceutically acceptable salt" relates to a salt which is cosmetically or pharmaceutically acceptable as defined herein, and which possesses the pharmaceutical and cosmetic properties and activity of the original compound.

It can be: (1) acid addition salts formed with inorganic acids such as hydrochloric acid, bromhydric acid, sulphuric acid, nitric acid, phosphoric acid or the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and the like, and (2) salts formed when an acid proton present in the parent compound is either replaced by a metal ion, e.g., an alkali metal ion (e.g., $Na^+$, $K^+$ or $Li^+$), an alkaline-earth metal ion (like $Ca^{2+}$ or $Mg^{2+}$) or an aluminium ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide. The cosmetically or pharmaceutically acceptable salt can be in particular a hydrochloride.

"stereoisomers" refers to configurational stereoisomers and includes geometric isomers and optical isomers.

The geometric isomers, also called E/Z isomers or cis-trans isomers, result from the different position of substituents on a double C=C bond which can have a Z or E configuration, also called cis or trans configuration.

The optical isomers result from the different position in space of substituents or lone pair of electrons on an atom (such as a carbon or sulphur atom) comprising four different substituents (including potentially a lone pair of electron). This atom thus represents a chiral or asymmetric center. Optical isomers which are not mirror images of one another are thus designated as "diastereoisomers" and optical isomers which are non-superimposable mirror images are designated as "enantiomers".

An equimolar mixture of two enantiomers of a chiral compound is designated as racemate or racemic mixture.

"($C_1$-$C_6$)alkyl" refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

"($C_2$-$C_6$)alkenyl" refers to a straight or branched unsaturated hydrocarbon chain containing from 2 to 6 carbon atoms and comprising at least one double bond including, but not limited to, ethenyl, propenyl, butenyl, pentenyl, hexenyl and the like.

"($C_2$-$C_6$)alkynyl" refers to a straight or branched unsaturated hydrocarbon chain containing from 2 to 6 carbon atoms and comprising at least one triple bond including, but not limited to, ethynyl, propynyl, butynyl, pentynyl, hexynyl and the like.

"($C_1$-$C_6$)alkoxy" refers to a ($C_1$-$C_6$)alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

"($C_3$-$C_7$)cycloalkyl" refers to a hydrocarbon ring having 3 to 7 carbon atoms including, but not limited to, cyclopropyl, cyclopentyl, cyclohexyl and the like.

"($C_3$-$C_7$)cycloalkyl-($C_1$-$C_6$)alkyl" refers to a ($C_3$-$C_7$)cycloalkyl group as defined above bound to the molecule via a ($C_1$-$C_6$)alkyl group as defined above. Advantageously, a ($C_3$-$C_7$)cycloalkyl-($C_1$-$C_6$)alkyl group comprises a cyclopropyl, cyclopentyl or cyclohexyl moiety and a methyl or ethyl moiety.

"aryl" refers to an aromatic hydrocarbon group comprising preferably 6 to 10 carbon atoms and comprising one or more fused rings, such as, for example, a phenyl or naphtyl group.

"aryl-($C_1$-$C_6$)alkyl" refers to an aryl group as defined above bound to the molecule via a ($C_1$-$C_6$)alkyl group as defined above. In particular, an aryl-($C_1$-$C_6$)alkyl group is a benzyl group.

"($C_1$-$C_6$)alkyl-aryl" refers to a ($C_1$-$C_6$)alkyl group as defined above bound to the molecule via an aryl group as defined above. In particular, a ($C_1$-$C_6$)alkyl-aryl group is a methyl-phenyl group.

"5- to 7-membered heterocycloalkyl" refers to a saturated hydrocarbon cycle having 5 to 7 members and in which one or several, notably 1 to 3, such as 1 or 2, carbon atoms are each replaced with a nitrogen, oxygen or sulphur atom, preferably with a nitrogen or oxygen atom. It can be for example a pyrrolidinyl, tetrahydrofuranyl, tetrahydrothienyl, piperidinyl, tetrahydropyranyl, morpholinyl, piperazinyl or azepanyl group.

"(5- to 7-membered heterocycloalkyl)-($C_1$-$C_6$)alkyl" refers to a 5- to 7-membered heterocycloalkyl group as defined above bound to the molecule via a ($C_1$-$C_6$)alkyl group as defined above. A (5- to 7-membered heterocycloalkyl)-($C_1$-$C_6$)alkyl group can comprise for example a pyrrolidinyl, tetrahydrofuranyl, tetrahydrothienyl, piperidinyl, tetrahydropyranyl, morpholinyl, piperazinyl or azepanyl moiety and a methyl or ethyl moiety.

"heteroaryl" refers to an aromatic group, having preferably 5 to 10 members, comprising one or more, notably one or two fused rings, in which the atoms of the ring(s) consist of one or more, advantageously 1 to 4, and more advantageously 1 or 2, heteroatoms selected from nitrogen, oxygen and sulphur atoms, the remainder being carbon atoms. A heteroaryl group can be notably thienyl, furanyl, pyrrolyl, indolyl, etc.

"heteroaryl-($C_1$-$C_6$)alkyl" refers to a heteroaryl group as defined above bound to the molecule via a ($C_1$-$C_6$)alkyl group as defined above. A heteroaryl-($C_1$-$C_6$)alkyl group can comprise for example a thienyl, furanyl, pyrrolyl or indolyl moiety and a methyl or ethyl moiety.

"trialkylsilyl" refers to a group —$SiAlk_1Alk_2Alk_3$ in which $Alk_1$, $Alk_2$ and $Alk_3$, identical or different, represent a ($C_1$-$C_6$)-alkyl group as defined above. For example, it can be a trimethylsilyl or triethylsilyl group.

"halogen" refers to a fluorine, bromine, chlorine or iodine atom.

"protecting group" refers to a chemical group which selectively blocks a reactive site in a multifunctional compound so as to allow selectively performing a chemical reaction on another unprotected reactive site.

"O-Protecting group" refers to a substituent which protects hydroxyl groups (OH) against undesirable reactions during synthetic procedures such as those O-protecting groups disclosed in "Greene's Protective Groups In Organic Synthesis", 4$^{th}$ edition, 2007, John Wiley & Sons, Hoboken, N.J. A hydroxyl group protected by a O-protecting group can be for example an ether, an ester, a carbonate, an acetal and the like. In particular, O-protecting groups can be a $(C_1-C_6)$alkyl optionally substituted with one or several (notably 1 to 3) halogen atoms (such as chlorine atoms), such as methyl, ethyl, tert-butyl or 2,2,2-trichloroethyl; an aryl-$(C_1-C_6)$alkyl, such as a benzyl, the aryl moiety being optionally substituted with one or several methoxy groups, such as benzyl (Bn) or p-methoxybenzyl (PMB); a trityl derivative of formula —$CAr_1Ar_2Ar_3$ such as triphenylmethyl (also called trityl—Tr), (4-methoxyphenyl)diphenylmethyl (also called methoxytrityl—NMT) or bis-(4-methoxyphenyl)phenylmethyl (also called dimethoxytrityl—DMT); a substituted methyl group of formula —$CH_2OR_{GP2}$ or —$CH_2SR_{GP2}$ (in particular —$CH_2OR_{GP2}$), for example, methoxymethyl (MOM), benzyloxymethyl, 2-methoxyethoxymethyl (MEM), 2-(trimethylsilyl) ethoxymethyl or methylthiomethyl; a substituted ethyl group of formula —$CH_2CH_2OR_{GP2}$ or —$CH_2CH_2SR_{GP2}$ (in particular —$CH_2CH_2OR_{GP2}$), for example, ethoxyethyl (EE); a silyl group of formula —$SiR_{GP3}R_{GP4}R_{GP5}$, for example, trimethylsilyl (TMS), triethylsilyl (TES), t-butyldimethylsilyl (TBS or TBDMS) and t-butyldiphenylsilyl (TBDPS); a carbonylated group of formula —CO—$R_{GP6}$ such as acetyl (Ac), pivaloyl (Piv or Pv) or benzoyl (Bz) or of formula —$CO_2$—$R_{GP7}$ such as allyloxycarbonyl (Alloc) or 9-fluorenylmethyloxycarbonyl (Fmoc); or a tetrahydropyranyl

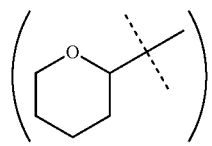

(THP) or tetrahydrofuranyl

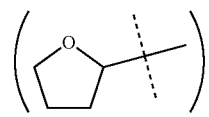

group; with $Ar_1$, $Ar_2$ and $Ar_3$ representing, independently from one another, an aryl, such as a phenyl, optionally substituted with one or several methoxy groups; $R_{GP2}$ representing a $(C_1-C_6)$alkyl (such as methyl or ethyl) optionally substituted with an aryl (such as phenyl), a $(C_1-C_6)$ alkoxy (such as methoxy) or a trialkylsilyl group (such as $SiMe_3$); $R_{GP3}$, $R_{GP4}$ and $R_{GP5}$ representing, independently from one another, a $(C_1-C_6)$alkyl or aryl (such as phenyl) group; and $R_{GP6}$ and $R_{GP7}$ representing, independently of each other, a $(C_1-C_6)$alkyl, a $(C_2-C_6)$alkenyl, an aryl, an aryl-$(C_1-C_6)$alkyl or a 9-fluorenylmethyl group. In particular, it will be a methyl, benzyl, acetyl or methoxymethyl group. More particularly, it can be a benzyl group.

"N-protecting group" refers to groups intended to protect an amine function (notably a primary amine function) against undesirable reactions during synthetic procedures. Commonly used N-protecting groups are disclosed in "Greene's Protective Groups In Organic Synthesis", 4$^{th}$ edition, 2007, John Wiley & Sons, Hoboken, N.J. An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups can be formyl; an aryl, such as a phenyl, optionally substituted with one or several methoxy groups such as p-methoxyphenyl (PMP); an aryl-$(C_1-C_6)$alkyl, such as a benzyl, the aryl moiety being optionally substituted with one or several methoxy groups, such as benzyl (Bn), p-methoxybenzyl (PMB) or 3,4-dimethoxybenzyl (DMPM); —CO—$R_{GP1}$ such as acetyl (Ac), pivaloyl (Piv or Pv), benzoyl (Bz) or p-methoxybenzylcarbonyl (Moz); —$CO_2$—$R_{GP1}$ such as tbutyloxycarbonyl (Boc), trichloroethoxycarbonyl (TROC), allyloxycarbonyl (Alloc), benzyloxycarbonyl (Cbz or Z) or 9-fluorenylmethyloxycarbonyl (Fmoc); —$SO_2$—$R_{GP1}$ such as phenylsulfonyl, tosyl (Ts or Tos) or 2-nitrobenzenesulfonyl (also called nosyl—Nos or Ns); and the like, with $R_{GP1}$ representing a $(C_1-C_6)$alkyl optionally substituted with one or several halogen atoms such as F or Cl; a $(C_2-C_6)$alkenyl such as an allyl; an aryl, such as a phenyl, optionally substituted with one or several groups chosen among OMe (methoxy) and $NO_2$ (nitro); an aryl-$(C_1-C_6)$alkyl, such as a benzyl, the aryl moiety being optionally substituted with one or several methoxy groups; or a 9-fluorenylmethyl group. In particular, it can be a t-butyloxycarbonyl, benzyloxycarbonyl or 9-fluorenylmethyloxycarbonyl group.

According to a first particular embodiment, the compound according to the invention is a compound having the following formula Ia:

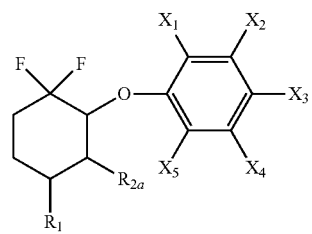

or a cosmetically or pharmaceutically acceptable salt thereof, a stereoisomer or a mixture of stereoisomers in any proportion, particularly an enantiomer or a mixture of enantiomers, and more particularly a racemate mixture, wherein $R_1$, $X_1$, $X_2$, $X_3$, $X_4$ and $X_5$ are as defined above or below and $R_{2a}$ represents OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$, with $R_{13}$ to $R_{22}$ as defined above or below. Thus, $R_{2a}$ is a $R_2$ group with $R_2$=OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$.

According to a second particular embodiment, the compound according to the invention is a compound having the following formula Ib:

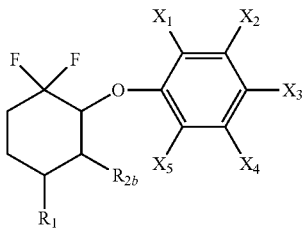

or a cosmetically or pharmaceutically acceptable salt thereof, a stereoisomer or a mixture of stereoisomers in any proportion, particularly an enantiomer or a mixture of enantiomers, and more particularly a racemate mixture, wherein $R_1$, $X_1$, $X_2$, $X_3$, $X_4$ and $X_5$ are as defined above or below and $R_{2b}$ represents $NH_2$, $NHR_{33}$, or $NR_{33}R_{34}$, with $R_{33}$ and $R_{34}$ as defined above or below. Thus, $R_{2b}$ is a $R_2$ group with $R_2$=$NH_2$, $NHR_{33}$, or $NR_{33}R_{34}$.

Advantageously, $X_1$, $X_2$, $X_3$, $X_4$ and $X_5$ represent, independently from one another, a hydrogen atom, OH, $OR_{26}$, $OC(O)R_{27}$, $OCO_2R_{28}$, or $OC(O)NR_{29}R_{30}$; preferably a hydrogen atom, OH or $OR_{26}$.

In particular, at least one of $X_1$, $X_2$, $X_3$, $X_4$ and $X_5$, and preferably $X_3$, represents a group other than a hydrogen atom, such as OH, $OR_{26}$, $OC(O)R_{27}$, $OCO_2R_{28}$, or $OC(O)NR_{29}R_{30}$, in particular such as OH or $OR_{26}$.

More particularly, $X_1$, $X_2$, $X_4$ and $X_5$ each represent a hydrogen atom and $X_3$ represents a group other than a hydrogen atom, i.e. OH, $OSiR_{23}R_{24}R_{25}$, $OR_{26}$, $OC(O)R_{27}$, $OCO_2R_{28}$, $OC(O)NR_{29}R_{30}$, $OP(O)(OR_{31})_2$, or $OSO_3R_{32}$; notably OH, $OR_{26}$, $OC(O)R_{27}$, $OCO_2R_{28}$, or $OC(O)NR_{29}R_{30}$; in particular OH or $OR_{26}$.

Advantageously, $R_1$ represents a hydrogen atom, OH, $OR_6$, $OC(O)R_7$, $OCO_2R_8$ or $OC(O)NR_9R_{10}$; more particularly a hydrogen atom, OH or $OR_6$.

Advantageously, $R_2$ represents $NH_2$, $NHR_{33}$, $NR_{33}R_{34}$, OH, $OR_{16}$, $OC(O)R_{17}$, $OCO_2R_{18}$ or $OC(O)NR_{19}R_{20}$; in particular $NH_2$, $NHR_{33}$, $NR_{33}R_{34}$, OH or $OR_{16}$; more particularly $NH_2$, OH or $OR_{16}$, e.g. $NH_2$ or OH. $R_2$ can represent in particular OH, $OR_{16}$, $OC(O)R_{17}$, $OCO_2R_{18}$ or $OC(O)NR_{19}R_{20}$; more particularly OH or $OR_{16}$, e.g. OH.

According to a particular embodiment:
$R_1$ represents a hydrogen atom, OH, $OR_6$, $OC(O)R_7$, $OCO_2R_8$ or $OC(O)NR_9R_{10}$, and
$R_2$ represents $NH_2$, $NHR_{33}$, $NR_{33}R_{34}$, OH, $OR_{16}$, $OC(O)R_{17}$, $OCO_2R_{18}$ or $OC(O)NR_{19}R_{20}$; in particular OH, $OR_{16}$, $OC(O)R_{17}$, $OCO_2R_{18}$ or $OC(O)NR_{19}R_{20}$.

According to another particular embodiment:
$R_1$ represents a hydrogen atom, OH or $OR_6$, and
$R_2$ represents $NH_2$, $NHR_{33}$, $NR_{33}R_{34}$, OH or $OR_{16}$; more particularly $NH_2$, OH or $OR_{16}$; in particular OH or $OR_{16}$.

According to a particular embodiment, $R_1$ does not represent a hydrogen atom.

In a preferred embodiment of the invention:
$X_1$, $X_2$, $X_4$, $X_5$ are identical and represent a hydrogen atom,
$X_3$ represents OH, $OSiR_{23}R_{24}R_{25}$, $OR_{26}$, $OC(O)R_{27}$, $OCO_2R_{28}$, $OC(O)NR_{29}R_{30}$, $OP(O)(OR_{31})_2$, or $OSO_3R_{32}$,
$R_1$ represents a hydrogen atom, OH, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$, and
$R_2$ represents $NH_2$, $NHR_{33}$, $NR_{33}R_{34}$, OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$; in particular OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$.

In another preferred embodiment of the invention:
$X_1$, $X_2$, $X_4$, $X_5$ are identical and represent a hydrogen atom,
$X_3$ represents OH, $OR_{26}$, $OC(O)R_{27}$, $OCO_2R_{28}$ or $OC(O)NR_{29}R_{30}$,
$R_1$ represents a hydrogen atom, OH, $OR_6$, $OC(O)R_7$, $OCO_2R_8$ or $OC(O)NR_9R_{10}$, and
$R_2$ represents $NH_2$, $NHR_{33}$, $NR_{33}R_{34}$, OH, $OR_{16}$, $OC(O)R_{17}$, $OCO_2R_{18}$ or $OC(O)NR_{19}R_{20}$; in particular OH, $OR_{16}$, $OC(O)R_{17}$, $OCO_2R_{18}$ or $OC(O)NR_{19}R_{20}$.

In a more preferred embodiment of this invention:
$X_1$, $X_2$, $X_4$, $X_5$ are identical and represent a hydrogen atom,
$X_3$ represents a OH or a $OR_{26}$, e.g. OH,
$R_1$ represents a hydrogen atom, a OH or a $OR_6$, e.g. H or OH, and
$R_2$ represents $NH_2$, $NHR_{33}$, $NR_{33}R_{34}$, OH or $OR_{16}$; more particularly $NH_2$, OH or $OR_{16}$; in particular OH or $OR_{16}$, e.g. OH.

According to a particularly advantageous embodiment:
$X_1$, $X_2$, $X_4$, $X_5$ are identical and represent a hydrogen atom, and
$X_3$, $R_1$ and $R_2$ are identical and represent a OH.

According to another particularly advantageous embodiment:
$X_1$, $X_2$, $X_4$, $X_5$ are identical and represent a hydrogen atom,
$X_3$ and $R_2$ are identical and represent a OH, and
$R_1$ represents a hydrogen atom.

According to another particularly advantageous embodiment:
$X_1$, $X_2$, $X_4$, $X_5$ are identical and represent a hydrogen atom,
$X_3$ represents a OH,
$R_2$ represents $NH_2$, and
$R_1$ represents a hydrogen atom.

In particular, in the definitions of $X_1$, $X_2$, $X_3$, $X_4$, $X_5$, $R_1$ and $R_2$ above:
$R_6$, $R_7$, $R_8$, $R_{16}$, $R_{17}$, $R_{18}$, $R_{26}$, $R_{27}$ and $R_{28}$ represent, independently from one another, a $(C_1-C_6)$alkyl, aryl, heteroaryl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group,
$R_9$, $R_{10}$, $R_{19}$, $R_{20}$, $R_{29}$ and $R_{30}$ represent, independently from one another, a hydrogen atom, or a $(C_1-C_6)$alkyl, aryl, heteroaryl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, and
$R_{33}$ and $R_{34}$ representing, independently from one another, a $(C_1-C_6)$alkyl, aryl, heteroaryl, aryl-$(C_1-C_6)$alkyl or heteroaryl-$(C_1-C_6)$alkyl group, said group being optionally substituted by one or several groups selected from a halogen atom, OH, COOH and CHO.

More particularly, in the definitions of $X_1$, $X_2$, $X_3$, $X_4$, $X_5$, $R_1$ and $R_2$ above:

- $R_6$, $R_7$, $R_8$, $R_{16}$, $R_{17}$, $R_{18}$, $R_{26}$, $R_{27}$ and $R_{28}$ represent, independently from one another, a ($C_1$-$C_6$)alkyl, aryl or aryl-($C_1$-$C_6$)alkyl group, said group being optionally substituted by one or several groups selected from a halogen atom, a ($C_1$-$C_6$)alkyl group and a ($C_1$-$C_6$)alkoxy group,
- $R_9$, $R_{10}$, $R_{19}$, $R_{20}$, $R_{29}$ and $R_{30}$ represent, independently from one another, a hydrogen atom, or a ($C_1$-$C_6$)alkyl, aryl or aryl-($C_1$-$C_6$)alkyl group, said group being optionally substituted by one or several groups selected from a halogen atom, a ($C_1$-$C_6$)alkyl group and a ($C_1$-$C_6$)alkoxy group, and
- $R_{33}$ and $R_{34}$ representing, independently from one another, a ($C_1$-$C_6$)alkyl, aryl or aryl-($C_1$-$C_6$)alkyl group, said group being optionally substituted by one or several groups selected from a halogen atom, OH, COOH and CHO.

Preferably, in the definitions of $X_1$, $X_2$, $X_3$, $X_4$, $X_5$, $R_1$ and $R_2$ above:

- $R_6$, $R_7$, $R_8$, $R_{16}$, $R_{17}$, $R_{18}$, $R_{26}$, $R_{27}$, $R_{28}$, $R_{33}$ and $R_{34}$ represent, independently from one another, a ($C_1$-$C_6$)alkyl, aryl or aryl-($C_1$-$C_6$)alkyl group, and
- $R_9$, $R_{10}$, $R_{19}$, $R_{20}$, $R_{29}$ and $R_{30}$ represent, independently from one another, a hydrogen atom, or a ($C_1$-$C_6$)alkyl, aryl or aryl-($C_1$-$C_6$)alkyl group.

The compound according to the invention can be chosen among:

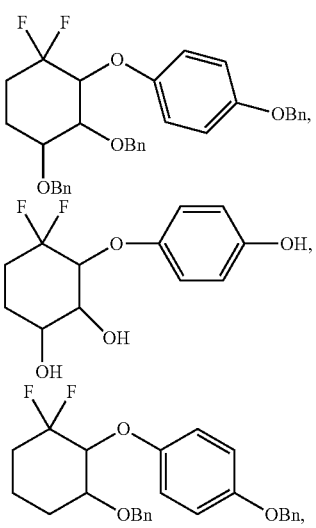

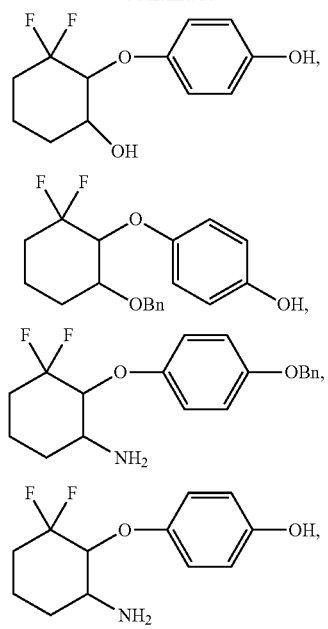

and cosmetically or pharmaceutically acceptable salts thereof.

The compound according to the invention can advantageously be chosen among: exemplified compounds 7, 8, 15, 16, 16a, 16b, 21, 26a, 26b, 28a, 28b and cosmetically or pharmaceutically acceptable salts thereof, notably exemplified compounds 7, 8, 15, 16 and cosmetically or pharmaceutically acceptable salts thereof, preferably chosen among exemplified compounds 8, 16, 16a, 16b, 28a, 28b and cosmetically or pharmaceutically acceptable salts thereof, notably exemplified compounds 8, 16 and cosmetically or pharmaceutically acceptable salts thereof.

Examples of cosmetically or pharmaceutically acceptable salts are compounds 27a and 27b which are hydrochloride salts of 28a and 28b respectively.

This invention also relates to processes for preparing a compound of formula I or a cosmetically or pharmaceutically acceptable salt thereof.

A particular process to prepare a compound of formula I is described in scheme 1.

Scheme 1

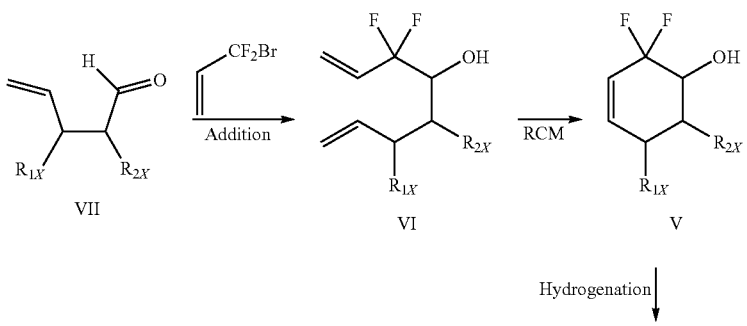

-continued

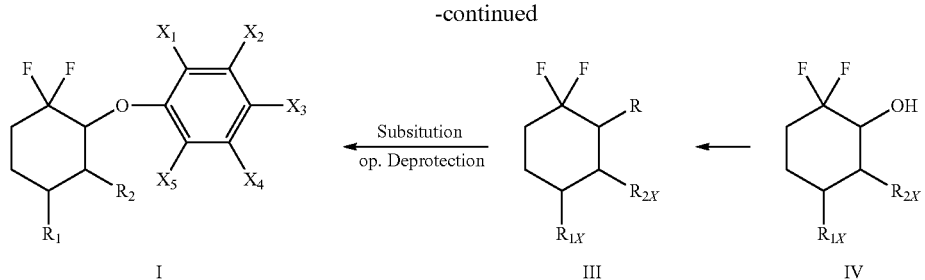

I   III   IV

The compounds of formula I wherein $X_1$, $X_2$, $X_3$, $X_4$, $X_5$, $R_1$, $R_2$ are as defined above and $R_2$ and the phenyloxy substituent are in the cis-configuration, can be prepared by a nucleophilic substitution between a compound of formula II and a compound of formula III

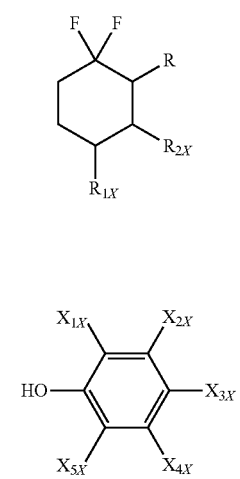

III

II wherein $X_{1X}$, $X_{2X}$, $X_{3X}$, $X_{4X}$, $X_{5X}$, $R_{1X}$ and $R_{2X}$ represent respectively $X_1$, $X_2$, $X_3$, $X_4$, $X_5$, $R_1$ and $R_2$ as defined above, optionally in a protected form, and R represents a leaving group.

The term "leaving group" as used in the present invention refers to a chemical group which can be easily replaced with a nucleophile during a nucleophile substitution reaction, the nucleophile being in the present case an alcohol, i.e. a molecule carrying a group OH. Such a leaving group can be in particular a sulfonate. The sulfonate is in particular a group —$OSO_2$—$R_{LG}$ with $R_{LG}$ representing a ($C_1$-$C_6$)alkyl, aryl, aryl-($C_1$-$C_6$)alkyl or ($C_1$-$C_6$)alkyl-aryl group, the said group being optionally substituted with one or several halogen atoms such as fluorine atoms. The sulfonate can be notably a mesylate ($CH_3$—$S(O_2)O$—), a triflate ($CF_3$—$S(O)_2O$—) or a tosylate (p-Me-$C_6H_4$—$S(O)_2O$—), in particular a triflate.

The nucleophilic substitution can be realized for example in dimethylformamide and in presence of a base such as $K_2CO_3$ or NaH, preferentially with $K_2CO_3$.

at least one of $X_{1X}$, $X_{2X}$, $X_{3X}$, $X_{4X}$, $X_{5X}$, $R_{1X}$, and $R_{2X}$ is in a protected form, one or several deprotection steps can be necessary. The conditions of deprotection are well-known to the one skilled in the art (e.g. "Greene's Protective Groups In Organic Synthesis", 4th edition, 2007, John Wiley & Sons, Hoboken, N.J.).

The protected group(s) can be in particular OH group(s), which can be protected with any O-protecting group such as defined previously, in particular a benzyl group. The protected group(s) can be also $NH_2$ group(s), which can be protected with any N-protecting group such as defined previously, in particular a Cbz group.

The compounds of formula II are commercially available or prepared with well-known synthesis methods.

The compounds of formula III can be obtained from a compound IV by the conversion of the hydroxyl group into a good leaving group R by methods well-known to the one skilled in the art.

The compounds of formula IV can be prepared from a compound V under hydrogenation condition. In this case, the double bond can be reduced by using hydrogen and palladium on carbon as catalyst, notably in ethyl acetate as solvent. The reaction can be carried out in the presence of triethylamine.

The compounds of formula V can be generated by ring closing metathesis (RCM) from a diene compound VI. The reaction can be conducted in the presence of Grubbs' catalyst (preferably of second generation), notably in toluene as solvent.

The compounds of formula VI can be formed by addition of 3-bromo-3,3-difluoropropene on a carbonyl compound VII in the presence of metal. For example, the metal can be indium, zinc, cadmium or tin. Particularly, the metal is indium. This step can be carried out in tetrahydrofuran/water (THF/$H_2O$) as solvent.

Another process for preparing a compound of formula I is described in scheme 2.

Scheme 2

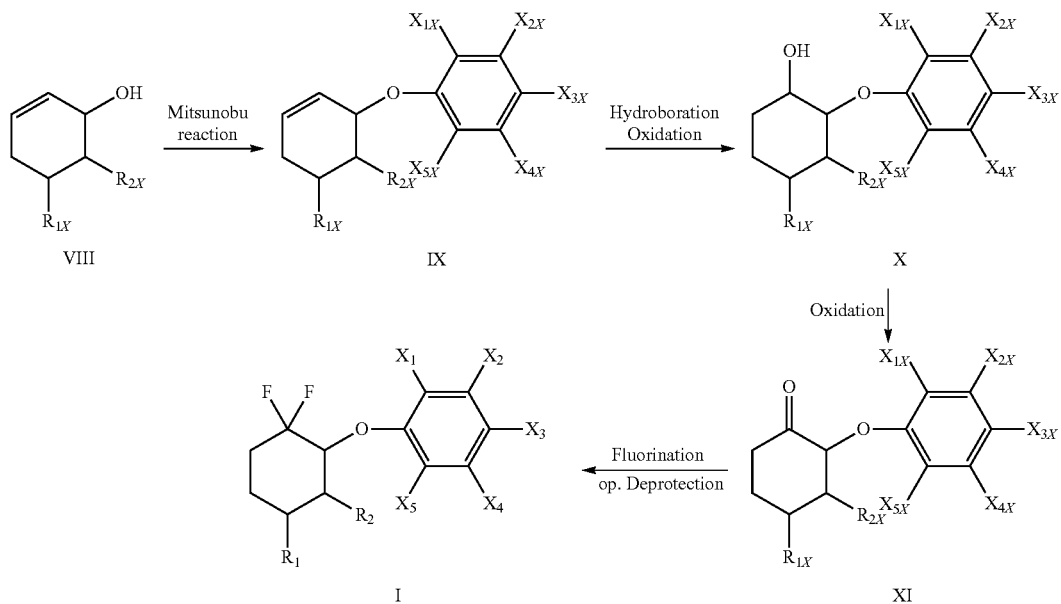

The compounds of formula I wherein $X_1$, $X_2$, $X_3$, $X_4$, $X_5$, $R_1$, $R_2$ are as defined above, can be obtained by a fluorination reaction of compounds of formula XI

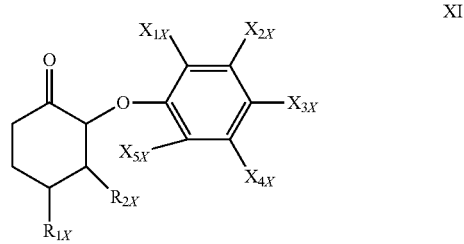

XI wherein $X_{1X}$, $X_{2X}$, $X_{3X}$, $X_{4X}$, $X_{5X}$, $R_{1X}$ and $R_{2X}$ are as defined previously.
The fluorinated agent can be for example DAST (diethylaminosulfur trifluoride). The fluorination reaction can be carried out in dichloromethane.
When at least one of $X_{1X}$, $X_{2X}$, $X_{3X}$, $X_{4X}$, $R_{1X}$, and $R_{2X}$ is in a protected form, one or several deprotection steps can be necessary. The conditions of deprotection are well-known to the one skilled in the art (e.g. "Greene's Protective Groups In Organic Synthesis", $4^{th}$ edition, 2007, John Wiley & Sons, Hoboken, N.J.).

The compounds of formula XI can be prepared by oxidation of compounds of formula X under oxidative conditions such as for example Dess Martin reagent, notably in dichloromethane.

The compounds of formula X can be prepared from compounds IX by a hydroboration-oxidation sequence. Such a reaction is well known to the one skilled in the art.

The compounds of formula IX can be obtained by Mitsunobu reaction between compounds of formula VIII and compounds of formula II described above. Such a reaction is well known to the one skilled in the art.

The compounds of formulas VII and VIII can be prepared with methods known to the person skilled in the art.

Another process for preparing a compound of formula I with $X_3$=OH is described in scheme 3.

Scheme 3

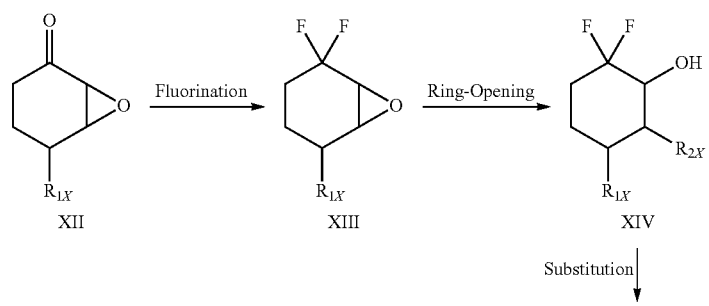

Substitution

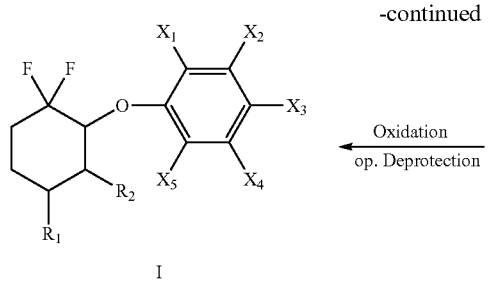

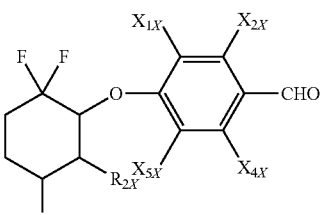

The compounds of formula I wherein $X_1$, $X_2$, $X_3$, $X_4$, $X_5$, $R_1$ are as defined above, $R_2$ is OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$, and $R_2$ and the phenyloxy substituent are in the trans-configuration, can be prepared by oxidation of aromatic aldehydes of formula XV

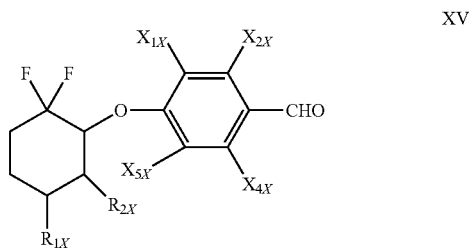

wherein $X_{1X}$, $X_{2X}$, $X_{4X}$, $X_{5X}$, $R_{1X}$ and $R_{2X}$ are as defined previously.

The oxidation can be performed by using Dakin reaction under the action of m-CPBA and NaOH.

When at least one of $X_{1X}$, $X_{2X}$, $X_{4X}$, $X_{5X}$, $R_{1X}$, and $R_{2X}$ is in a protected form, one or several deprotection steps can be necessary. The conditions of deprotection are well-known to the one skilled in the art (e.g. "Greene's Protective Groups In Organic Synthesis", 4$^{th}$ edition, 2007, John Wiley & Sons, Hoboken, N.J.).

The compounds of formula XV can be obtained by an aromatic nucleophilic substitution between a compound of formula XIV and a compound of formula XVI

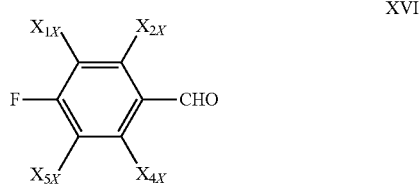

The nucleophilic substitution can be realized for example in dimethylformamide and in presence of a base such as $K_2CO_3$.

The compounds of formula XVI are commercially available or prepared with well-known synthesis methods.

The compounds of formula XIV can be generated by Ring-Opening of the epoxide compounds of formula XIII. The reaction can be conducted in the presence of an aromatic alcohol and a Lewis acid such as Erbium (III) triflate.

The compounds of formula XIII can be formed by a difluorination reaction of compounds of formula XII. The fluorinated agent can be DAST (diethylaminiosulfur trifluoride).

The compounds of formula XII are commercially available or prepared with well known synthesis methods.

Another process to prepare a compound of formula I is described in scheme 4.

Scheme 4

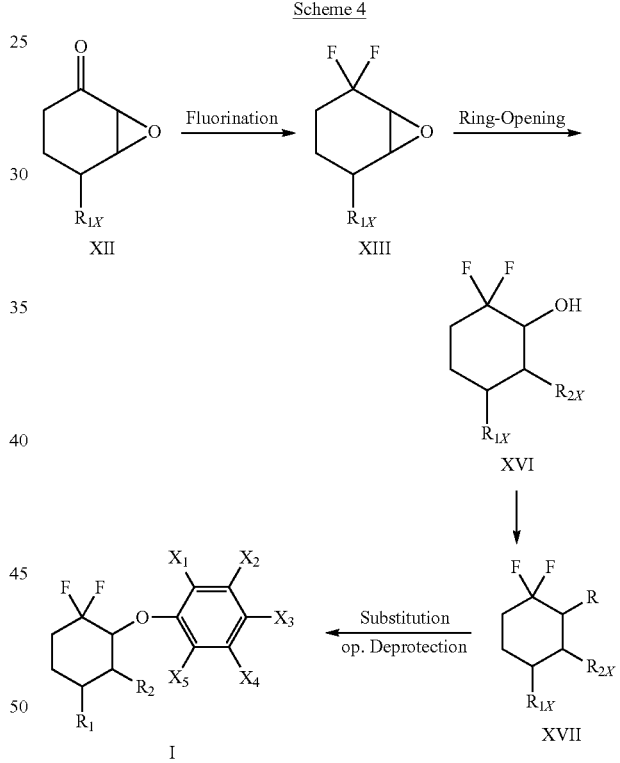

The compounds of formula I wherein $X_1$, $X_2$, $X_3$, $X_4$, $X_5$, $R_1$ are as defined above, $R_2$ is $NH_2$, $NHR_{33}$, or $NR_{33}R_{34}$, and $R_2$ and the phenyloxy substituent are in the cis-configuration, can be obtained by a nucleophilic substitution between a compound of formula II and a compound of formula XVII wherein $X_{1X}$, $X_{2X}$, $X_{3X}$, $X_{4X}$, $X_{5X}$, $R_{1X}$ are as defined previously, and R represents a leaving group, such as a sulfonate (e.g. triflate), and $R_{2X}$ represents $R_2$ as defined above, optionally in a protected form.

When at least one of $X_{1X}$, $X_{2X}$, $X_{3X}$, $X_{4X}$, $X_{5X}$, $R_{1X}$, and $R_{2X}$ is in a protected form, one or several deprotection steps can be necessary. The conditions of deprotection are well-known to the one skilled in the art (e.g. "Greene's Protective Groups In Organic Synthesis", 4$^{th}$ edition, 2007, John Wiley & Sons, Hoboken, N.J.).

The compounds of formula XVII can be obtained from a compound XVI by the conversion of the hydroxyl group into a good leaving group R (e.g. a sulfonate such as a triflate) by methods well-known to the one skilled in the art.

The compounds of formula XVI can be generated by Ring-Opening of the epoxides compounds of formula XIII. The reaction can be realized for example in the presence of an amine and trimethylaluminium.

The compound of formula XIII can be formed by a difluorination reaction of compounds of formula XII. The fluorinated agent can be DAST (diethylaminiosulfur trifluoride).

Protection and deprotection steps can be used during the four processes described above in order to prevent undesired reactions. These steps are well known by a person skilled in the art.

A final salification steps can be performed in both processes in order to prepare a cosmetically or pharmaceutically acceptable salt of the compound of formula I. Such a reaction can be carried out by mixing the compound of formula I with an appropriate acid or base, notably as defined above.

The compounds described in the present invention can be separated from the reaction medium by using methods well known to the person skilled in the art, for example by extraction, evaporation of the solvent, precipitation or crystallization followed by filtration.

The compounds can be purified for example by chromatography on a column of silica gel, a high performance liquid chromatography, a recristallization or a distillation.

The present invention relates also to a cosmetic or pharmaceutical composition, more particularly a cosmetic or dermatological composition, comprising at least one compound according to the invention and at least one cosmetically or pharmaceutically acceptable excipient.

Such a composition is more particularly intended to be applied topically, in particular on the skin, such as a human skin.

Such a composition can thus be in the form of a lotion, a foam, a gel, a dispersion, a suspension, a spray, a serum, a cream, an emulsion, a milk, and oil or a mask.

The composition of the invention can also comprise one or more additive(s), such as antioxidants, emollients, humectants, thickening agents, fragrances, preservatives, pigments or colorants, or opacifiers. Such additives are conventional to those of skill in the art.

Examples of these additives are listed below as well as in the International Cosmetic Ingredient Dictionary and Handbook, eds. Wenninger and McEwen (The Cosmetic, Toiletry, and Fragrance Assoc., Washington, D.C., 7@th Edition, 1997).

Antioxidants can be used to protect ingredients of the composition from oxidizing agents that are included within or come in contact with the composition. Examples of antioxidants include ascorbyl palmitate, butylated hydroxyanisole, butylated hydroxytoluene, potassium propyl gallate, octyl gallate, dodecyl gallate, phenyl-α-napthyl-amine, and tocopherols such as α-tocopherol.

Emollients are agents that soften and smooth the skin. Examples of emollients include oils and waxes such as siloxanes such as dimethicone and derivatives thereof, microcrystaline wax, polyethylene, triglyceride esters such as those of castor oil, cocoa butter, safflower oil, corn oil, olive oil, cod liver oil, almond oil, palm oil, squalene, and soybean oil, acetylated monoglycerides, ethoxylated glycerides, fatty acids, alkyl esters of fatty acids, alkenyl esters of fatty acids, fatty alcohols, fatty alcohol ethers, etheresters, lanolin and derivatives of lanolin, polyhydric alcohol esters, wax esters such as beeswax, vegetable waxes, phospholids, sterols, isopropyl palmitate or glyceryl stearate.

Humectants are used to increase and maintain moisture in the skin. Examples of humectants include propylene glycol, butylene glycol, polyethylene glycol (PEG) (such as PEG-4 to PEG-32), glycerol (also called glycerin), sorbitol, xylitol, maltitol, mannitol, polydextrose, hyaluronic acid and its salts (such as sodium or potassium salt), urea, aloe vera, honey, etc.

Thickening agents are used to increase the viscosity and thickness of the composition. Examples of thickening agents include lipid thickening agents such as Cetyl Alcohol, Stearyl Alcohol, Myristyl Alcohol, Carnauba Wax, or Stearic acid; naturally derived thickening agents such as Cellulose derivatives like Hydroxyethylcellulose, Guar gum, Locust Bean Gum, Xanthan Gum, or Gelatin; mineral thickening agents such as Silica, Bentonite, or Magnesium Aluminum Silicate; synthetic thickening agents such as Carbomer; ionic thickening agents such as NaCl.

Examples of fragrances or perfume include peppermint, rose oil, rose water, aloe vera, clove oil, menthol, camphor, *eucalyptus* oil, and other plant extracts. To eliminate certain odours from compositions, masking agents may be used.

Preservatives can be used to protect the composition from degradation. Examples of preservatives include phenoxyethanol, butylparaben, ethylparaben, methylparaben, propyl paraben, benzalkonium chloride, benzethonium chloride, benzoic acid, benzyl alcohol, and mixtures thereof such as liquipar oil. However, the composition of the present invention can be preservative free.

Pigments or colorants are used to modify the color of the composition, such as to obtain a white composition.

Opacifiers, such as titanium oxide, are used in clear or transparent composition in order to render it opaque. The present invention can thus be clear or opaque according to the use or not of an opacifier.

The present invention relates also to the cosmetic use of a compound according to the invention, in particular as depigmenting, lightening, bleaching or whitening agent, more particularly for the skin, such as a human skin.

The invention relates also to the cosmetic use of a cosmetic composition according to the invention, in particular as a depigmenting, lightening, bleaching or whitening composition, more particularly intended to be applied topically on the skin, such as a human skin.

The invention concerns also the use of a compound according to the invention for the preparation of a cosmetic composition, intended notably for depigmenting, lightening, bleaching or whitening the skin, such as a human skin.

The invention concerns also a compound according to the invention for use as a depigmenting, lightening, bleaching or whitening agent, more particularly for the skin, such as a human skin.

The invention concerns also a method for depigmenting, lightening, bleaching or whitening the skin, such as a human skin, by applying on said skin an efficient amount of a compound according to the invention or of a cosmetic composition according to the invention to a person in need thereof.

The present invention relates also to a compound according to the invention for use as a drug, notably in the treatment of pigmentation disorders, more particularly by topical application on the skin, such as a human skin.

The invention relates also to a pharmaceutical composition, in particular a dermatological composition, according to the invention for use as a drug, notably in the treatment of pigmentation disorders, more particularly by topical application on the skin, such as a human skin.

The invention concerns also the use of a compound according to the invention for the preparation of a pharmaceutical composition, in particular a dermatological composition, intended notably for the treatment of pigmentation disorders, more particularly by topical application on the skin, such as a human skin.

The invention concerns also the use of a compound according to the invention for the treatment of pigmentation disorders, more particularly by topical application on the skin, such as a human skin.

The invention concerns also a method for treating the pigmentation disorders of the skin, such as a human skin, by applying on said skin an efficient amount of a compound according to the invention or of a pharmaceutical composition, in particular a dermatological composition, according to the invention to a person in need thereof.

The pigmentation disorders will be more particularly a hyperpigmentation, notably resulting from overexposure to the sun, inflammation, injuries, burns, medicines or hormonal alteration, such as lentigo or melasma.

To illustrate the invention, examples of compounds preparation are described below. The list of examples is not intended to be limitative.

FIGURE

FIG. 1 represents the inhibition of human tyrosinase kinetics of compound 8 at 1.12 mM.

EXAMPLES

The following abbreviates have been used in the examples.
DAST: Diethylaminosulfur trifluoride
DBU: 1,8-Diazabicyclo[5.4.0]undec-7-ene
DCM: Dichloromethane
DMF: Dimethylformamide
eq.: equivalent
ESI: Electrospray ionisation
mCPBA: meta-Chloroperoxybenzoic acid
NMR: Nuclear Magnetic Resonance
rt: room temperature
sat. aq.: saturated aqueous
THF: Tetrahydrofuran 1. Preparation of the Compounds According to the Invention Synthesis of Intermediate Compound 2

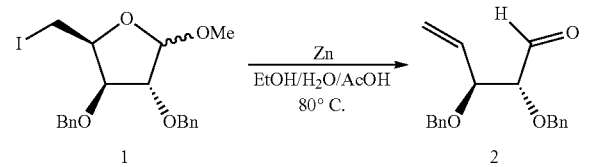

Under inert atmosphere, zinc (32.8 g, 501.9 mmol, 5 eq.) was added to a solution of compound 1 (prepared as described in J. Org. Chem. 2005, 70, 10139-10142) (45.6 g, 100.4 mmol, 1 eq.) in a mixture of ethanol (1.4 L)/water (70.2 mL)/AcOH (35.1 mL). The mixture was stirred at reflux for 1 h. Then the mixture was filtered over cotton to remove Zinc. The cotton was washed with ethyl acetate and the filtrate was concentrated, dissolved in ethyl acetate, washed with sat. aq. NaHCO$_3$, water, dried over sodium sulfate, filtered and concentrated to give intermediate compound 2 (29.6 g, 99%) as a yellowish oil.

$^1$H NMR (CDCl$_3$, 300 MHz): 3.8 (dd, J=1.5 Hz, J=3.9 Hz, 1H); 4.2 (dd, J=3.9 Hz, J=7.5 Hz, 1H); 4.4 (d, J=12 Hz, 1H); 4.6-4.7 (m, 2H); 4.8 (d, J=12 Hz, 1H); 5.3-5.4 (m, 2H); 6 (ddd, J=7.8 Hz, J=10.5 Hz, J=17.4 Hz, 1H); 7.3-7.4 (m, 10H); 9.7 (d, J=1.5 Hz, 1H).

Synthesis of Intermediate Compound 3

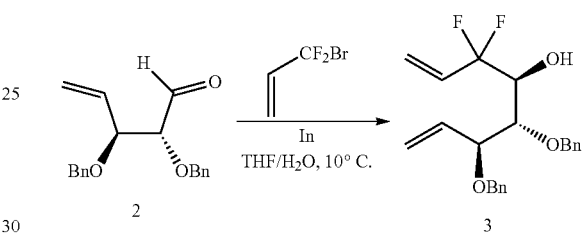

Under inert atmosphere, 3-bromo-3,3-difluoropropene (12.3 mL, 119 mmol, 1.2 eq.) was added to a cooled heterogeneous solution (10° C.) of intermediate compound 2 (29.6 g, 99.7 mmol, 1 eq.) in THF (55.4 mL)/H$_2$O (203 mL) and indium (13.7 g, 119 mmol, 1.2 eq.). The mixture was stirred at 10° C. for 1 hour. Then, HC12N was added and the mixture was extracted with Et$_2$O. The organic layers were combined, dried over sodium sulfate and concentrated. The crude oil was purified by silica gel chromatography (Biotage® SNAP 750 g, cyclohexane/ethyl acetate 100:0 to 73:17) to afford intermediate compound 3 (15.9 g, 43%) as a colorless oil.

Mass (ESI$^+$): 375.2[M+H]$^+$, 392.2[M+NH$_4$]$^+$, 397.2[M+Na]$^+$.

$^{19}$Fdec NMR (CDCl$_3$, 282.5 MHz): −108.2 (d, J=251 Hz, 1F); −113.4 (d, J=251 Hz, 1F).

Synthesis of Intermediate Compound 4

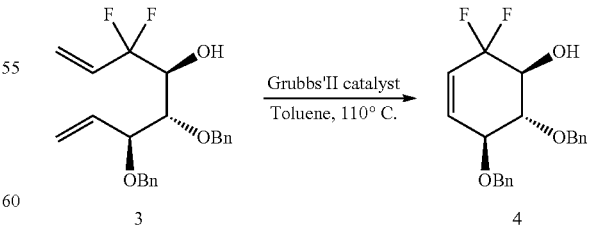

Under inert atmosphere, Grubbs'II catalyst (2.09 g, 2.46 mmol, 8%) was added to a degazed solution of intermediate compound 3 (11.5 g, 30.8 mmol, 1 eq.) in toluene (164 mL). The mixture was stirred under reflux for 1 hour, filtered over a pad of SiO$_2$ which was washed with ethyl acetate. The filtrate was concentrated and the crude compound was purified by silica gel chromatography (Biotage® SNAP 340 g, cyclohexane/ethyl acetate 100:0 to 80:20) to afford intermediate compound 4 (5.9 g, 58%) as a brown solid.

Mass (ESI+): 364.2 [M+NH4]+.

19Fdec NMR (CDCl3, 282.5 MHz): −102.4 (d, J=274 Hz, 1F); −105.2 (d, J=274 Hz, 1F).

Synthesis of Intermediate Compound 5

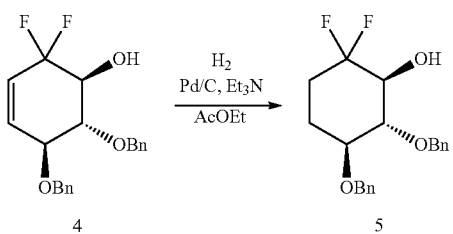

Et3N (0.6 mL, 4.33 mmol, 1.5 eq.) followed by 10% Pd/C (0.184 g, 0.173 mmol, 6%) were added to a solution of intermediate compound 4 (1.00 g, 2.89 mmol, 1 eq.) in ethyl acetate (72 mL). The mixture was stirred 2 hours under hydrogen atmosphere at room temperature, filtered on millipore 0.45 μm and concentrated. The crude compound was purified on silica gel chromatography (Biotage® ZIP 45 g, cyclohexane/ethyl acetate 100:0 to 70:30) to afford intermediate compound 5 (838 mg, 83%) as a white solid.

Mass (ESI+): 366.2[M+NH4]+, 371.1 [M+Na]+, 387.1 [M+K]+.

19Fdec NMR (CDCl3, 282.5 MHz): −106.4 (d, J=242 Hz, 1F); −116.3 (brd, 1F).

Synthesis of Intermediate Compound 6

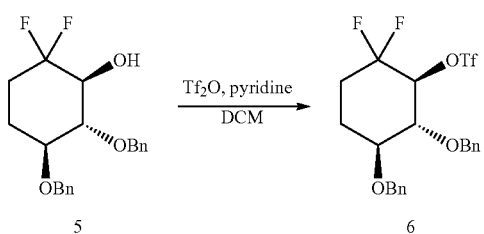

Pyridine (0.63 mL, 7.69 mmol, 4 eq) followed by trifluoromethanesulfonic anhydride (1.29 mL, 7.69 mmol, 4 eq) were added to a cooled solution (0° C.) of intermediate compound 5 (670 mg, 1.92 mmol, 1 eq.) in dichloromethane (17.9 mL) under inert atmosphere. The reaction mixture was stirred at room temperature for 16 hours. The mixture was then diluted with dichloromethane and washed twice with 2N HCl. The organic layer was dried over sodium sulfate and concentrated to give crude intermediate compound 6 (889 mg) as a dark residue. Intermediate compound 6 was engaged in the next step without further purification.

19F NMR (CDCl3, 282.5 MHz): −104.5 (dt, J=246 Hz, J=11 Hz, 1F); −115.5 (d, J=246 Hz, 1F).

Synthesis of Compound 7

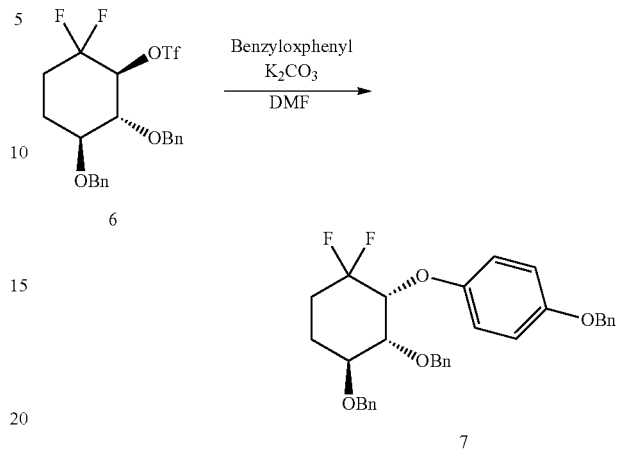

K2CO3 (0.673 g, 4.87 mmol, 3 eq.) and benzyloxyphenol (1.14 g, 5.68 mmol, 3.5 eq.) were dissolved in DMF (3.9 mL) under an inert atmosphere, and this suspension was stirred at room temperature for 1 h. A solution of intermediate compound 6 (0.78 g, 1.62 mmol, 1 eq.) in DMF (1.56 mL) was added, and the mixture was heated to 110° C. overnight. Water was then added and the aqueous layer was extracted twice with ethyl acetate. The combined organic layers were washed with brine, dried over sodium sulfate, and concentrated to give a dark oil. This crude material was purified by a flash chromatography (Biotage® ZIP 10 g, cyclohexane/ethyl acetate 100:0 to 87:13) to afford intermediate compound 7 (575 mg, 67%) as a yellowish oil.

Mass (ESI+): 548.3[M+NH4]+, 553.2[M+Na]+, 569.2[M+K]+.

Synthesis of Compound 8

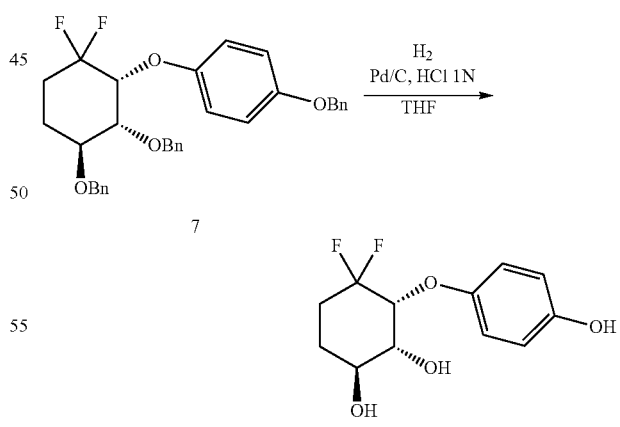

Pd/C 10% (128 mg, 0.12 mmol, 10%,) was added to a solution of compound 7 (637 mg, 1.2 mmol, 1 eq.) in THF (35 mL). Then, 1N HCl (4.8 mL, 4.8 mmol, 4 eq.) was added. The mixture was stirred for 2 hours under hydrogen atmosphere at room temperature. The reaction mixture was filtered (H-PTFE 0.45 m) and concentrated. The crude residue was purified by a flash chromatography (Biotage® SNAP 25 g, dichloromethane/methanol 100:0 to 90:10) to afford compound 8 (222 mg, 71%).

Mass(ESI⁻): 259.1[M−H]⁺.

$^{19}$Fdec (MeOD, 282.5 MHz): −104.7 (brd, J=257 Hz, 1F); −106.8 (brd, J=257 Hz, 1F).

Synthesis of Intermediate Compound 9

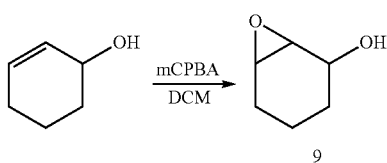 [SMILES: OC1C=CCCC1 ; OC1CCCC2OC12]

To a solution of cyclohex-2-enol in its racemic form (1.0 g, 9.68 mmol, 1 eq.) in DCM (70 mL) at 0° C. was added mCPBA (77%, 3.80 g, 16.9 mmol, 1.75 eq.). After stirring at room temperature for 16 h, the reaction mixture was washed with aqueous Na$_2$S$_2$O$_3$. The organic layer was then dried over sodium sulfate, filtered and concentrated to afford intermediate compound 9 (360 mg, 33%) as a crude residue.

$^1$H NMR (CDCl$_3$, 300 MHz): 1.00-2.00 (m, 6H); 3.32 (s, 1H); 3.35 (s, 1H); 4.01 (s, 1H).

Synthesis of Intermediate Compound 10

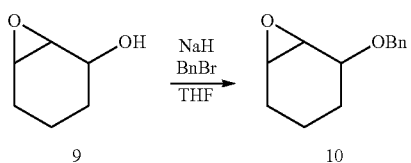 [SMILES: OC1CCCC2OC12 ; c1ccc(COC2CCCC3OC23)cc1 ; "THF"]

A solution of intermediate compound 9 (360 mg, 3.15 mmol, 1 eq.) in THF (4 mL) was added to a suspension of NaH (204 mg, 8.52 mmol, 2.7 eq.) and BnBr (0.377 mL, 3.15 mmol, 1 eq.) in THF at 55° C. After heating at 55° C. for 4 h, ice was slowly added to the mixture which was then extracted twice with Et$_2$O. The combined organic layers were then washed with brine, dried over sodium sulfate, filtered and concentrated. The crude residue was then purified by silica gel chromatography (Biotage® ZIP 5 g, cyclohexane/ethyl acetate 100:0 to 70:30) to afford 10 (413 mg, 64%) as a yellow liquid.

Mass (IC⁺): 205.2.

Synthesis of Intermediate Compound 11

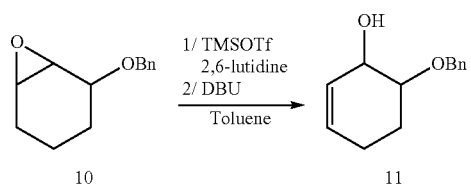 [SMILES: c1ccc(COC2CCCC3OC23)cc1 ; "Toluene" ; OC1C=CCCC1OCc1ccccc1]

A solution of intermediate compound 10 (410 mg, 2.00 mmol, 1 eq.) in toluene (12.6 mL) under inert atmosphere was treated with trimethylsilyltrifluoromethanesulfonate (TMSOTf) (0.38 mL, 2.11 mmol, 1.05 eq.) followed by 2,6-lutidine (1.17 mL, 10.0 mmol, 5 eq.). After stirring for 30 min at room temperature, DBU (1.50 mL, 10.0 mmol, 5 eq.) was added. The reaction mixture was then diluted with 2N HCl, extracted twice with Et$_2$O and the combined organic layers were washed with brine, dried over sodium sulfate, filtered and concentrated. The crude residue was purified by flash chromatography over silica gel (Biotage® ZIP 30 g, cyclohexane/ethyl acetate 100:0 to 70:30) to afford intermediate compound 11 (335 mg, 82%) as a yellow liquid.

$^1$H NMR (CDCl$_3$, 300 MHz): 1.54-2.60 (m, 4H); 2.39 (brs, 1H, OH); 3.65 (m, 1H); 4.22 (brs, 1H); 4.59 (d, 1H, J=11.7 Hz, OCHHPh); 4.63 (m, 1H); 4.68 (d, J=11.7 Hz, 1H, OCHHPh); 3.46 (m, 1H, CH=); 5.82 (m, 1H, CH=); 7.26-7.37 (m, 5H, HAr).

Synthesis of Intermediate Compound 12

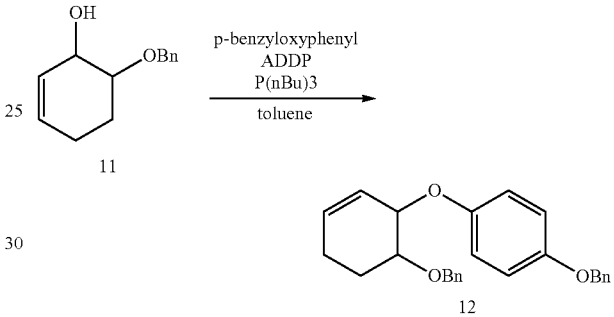

p-Benzyloxyphenol (348 mg, 1.70 mmol, 1.2 eq.) and 1,1'-(azodicarbonyl)dipiperidine (ADDP) (430 mg, 1.70 mmol, 1.2 eq.) were added to a solution of intermediate compound 11 (290 mg, 1.42 mmol, 1 eq.) in toluene (4.53 mL) under inert atmosphere. The mixture was cooled to 0° C. and P(nBu)$_3$ (0.45 mL, 1.70 mmol, 1.2 eq.) was added. The reaction mixture was then stirred at room temperature for 2 h before being diluted with DCM. The mixture was then concentrated and the crude residue was purified by flash chromatography over silica gel (Biotage® SNAP 50 g, cyclohexane/ethyl acetate 100:0 to 70:30) to afford intermediate compound 12 (382 mg, 70%) as a yellow oil.

Mass (ESI⁺): 404.2 [M+NH$_4$]⁺; 409.1 [M+Na]⁺; 425.1 [M+K]⁺.

Synthesis of Intermediate Compound 13

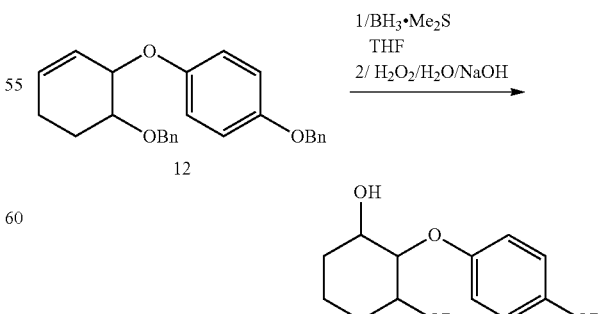

BH$_3$.Me$_2$S (2M in THF, 0.37 mL, 0.74 mmol, 5 eq.) was slowly added to a solution of intermediate compound 12 (57.0 mg, 0.15 mmol, 1 eq.) in THF (0.75 mL) cooled to 0° C. The mixture was then stirred at room temperature for 20 hours. The reaction mixture was then cooled to 0° C. and H$_2$O$_2$ (30% w/v, 0.45 mL, 4.42 mmol, 30 eq.), water (0.19 mL, 10.32 mmol, 70 eq.) and NaOH (2M in water, 0.59 mL, 1.18 mmol, 8 eq.) were successively added. The mixture was then stirred for an additionnal 3 h at room temperature. Water was added to the mixture which was then extracted 3 times with ethyl acetate. The combined organic layers were then dried over sodium sulfate, filtered and concentrated. The crude residue was purified by flash chromatography over silica gel (Biotage® ZIP 10 g, cyclohexane/ethyl acetate 95:5 to 60:40) to afford intermediate compound 13 (22 mg, 37%) as a colourless oil.

Mass (ESI$^+$): 422.3[M+NH$_4$]$^+$.

Synthesis of Intermediate Compound 14

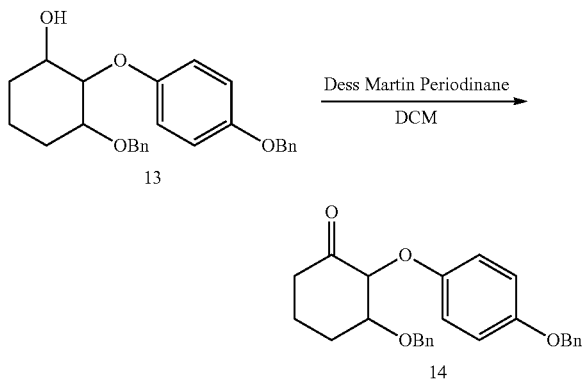

Dess Martin periodinane (34.6 mg, 0.08 mmol, 1.5 eq.) was added to a solution of intermediate compound 13 (22.0 mg, 0.05 mmol, 1 eq.) in DCM (0.16 mL). The reaction mixture was stirred at room temperature for 2 hours. NaOH (1M in water) was then added to the mixture which was then extracted 3 times with DCM. The combined organic layers were then dried over sodium sulfate, filtered and concentrated. The crude residue was purified by flash chromatography over silica gel (AIT 4 g, cyclohexane/ethyl acetate 93:7 to 40:60) to afford intermediate compound 14 (12 mg, 55%) as a colourless oil.

Mass (ESI$^+$): 420.2[M+NH$_4$]$^+$.

Synthesis of Compound 15

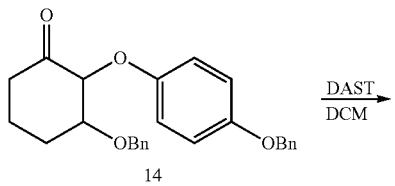

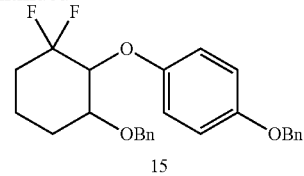

15

DAST (0.42 mL, 3.47 mmol, 10 eq.) was added to a solution of intermediate compound 14 (140 mg, 0.35 mmol, 1 eq.) in DCM (0.94 mL) under inert atmosphere. The mixture was stirred at room temperature for 2 hours before DCM was added. The diluted solution was then poured onto a cold aqueous solution of NaHCO$_3$. The mixture was stirred 5 min before being extracted 3 times with DCM. The combined organic layers were dried over sodium sulfate, filtered and concentrated. The crude residue was purified by flash chromatography over silica gel (Biotage® SNAP KP-Sil 10 g, cyclohexane/ethyl acetate 99:1 to 90:10) to afford compound 15 (77 mg, 52%) as a yellow oil.

Mass (ESI$^+$): 447.1 [M+Na]$^+$.

Synthesis of Compound 16

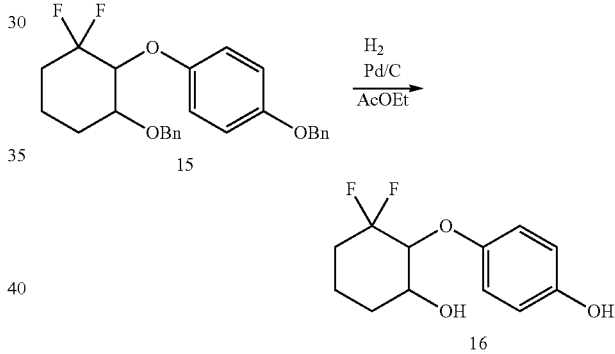

Pd/C (10%, 15.0 mg, 0.01 mmol, 0.3 eq.) was added to a solution of compound 15 (20 mg, 0.05 mmol, 1 eq) in ethyl acetate (1 mL) under inert atmosphere. The mixture was then stirred under hydrogen atmosphere (10 bars) overnight. The mixture was filtered (over Millipore 0.45 μm) and the filter was washed with ethyl acetate. The filtrate was finally concentrated to afford compound 16 as a white solid in a quantitative yield.

Mass (ESI$^-$): 243.1[M−H]$^+$.

$^{19}$Fdec (MeOD, 282.5 MHz): −100.0 (d, J=246 Hz, 1F); −113.9 (d, J=246 Hz, 1F).

The compound 16 was obtained as a racemate mixture of the two following enantiomers 16a and 16b.

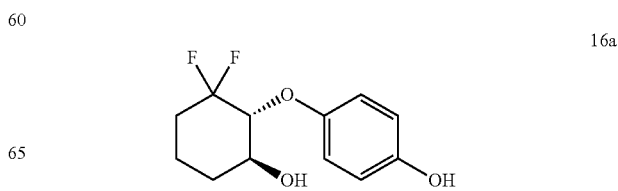

27

-continued

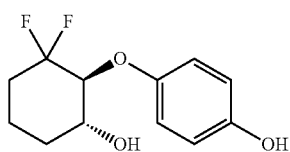

16b

Synthesis of Compound 18

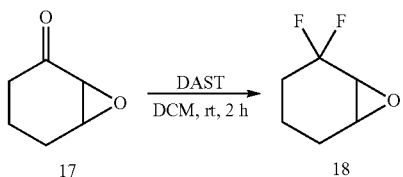

DAST (5 eq., 13.5 g, 10.3 mL, 83.9 mmol) was added to a solution of 7-oxabicyclo[4.1.0]heptan-2-one (1 eq., 1.92 g, 1.7 mL, 16.8 mmol) in dry DCM (17 mL) under inert atmosphere, at room temperature. The reaction mixture was stirred for 2 h before being poured onto a mixture of ice and water. The organic layer was then filtered through a plug of silica gel. DCM was slowly removed by distillation from 45° C. under atmospheric pressure to 85° C. under reduced pressure. Compound 18 (1.94 g, 86%) was obtained as a yellowish liquid.

[19]Fdec NMR (CDCl$_3$, 282.5 MHz): −96.5 (d, J=263 Hz, 1F); −100.2 (d, J=263 Hz, 1F).

Synthesis of Compound 19

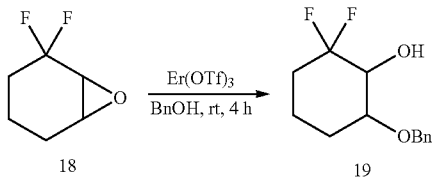 [SMILES: FC1(F)CCCC2OC21 ; OC1C(OCc2ccccc2)CCCC1(F)F ; "Er(OTf)3"]

Tris(trifluoromethanesulfonic acid) erbium (10%, 0.47 g, 0.746 mmol) was added to a solution of compound 18 (1 eq., 1 g, 7.46 mmol) in benzyl alcohol (935 µL, 8.95 mmol, 1.2 eq) and the mixture was stirred at room temperature for 4 h. A saturated solution of NaHCO$_3$ followed by DCM were added to the mixture which was extracted twice with DCM. The combined organic layer was dried over Na$_2$SO$_4$, filtered and concentrated. The crude residue was purified by a flash chromatography (Biotage®; AIT 120 g, cyclohexane/ethyl acetate 100:0 to 70:30) to afford compound 19 (935 mg, 3.86 mmol, 52%) as a yellowish solid.

Mass (ESI$^+$): 260.1 [M+NH$_4$]$^+$

[19]Fdec NMR (CDCl$_3$, 282.5 MHz): −104.1 (d, J=241 Hz, 1F); −118.0 (brd, J=241 Hz, 1F).

28

Synthesis of Compound 20

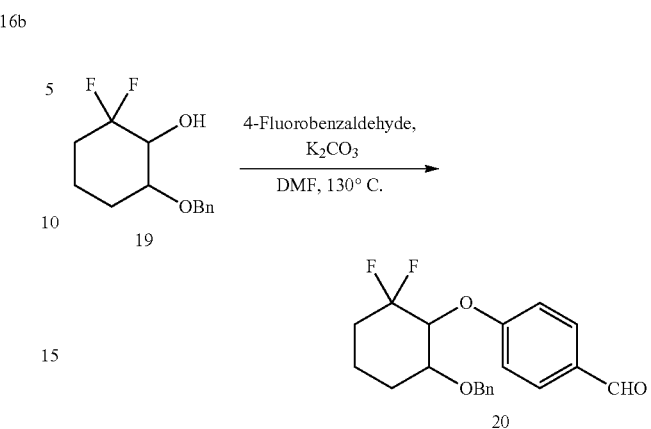

K$_2$CO$_3$ (6 eq., 222 mg, 1.61 mmol) was added to a solution of compound 19 (1 eq., 65 mg, 0.268 mmol) and 4-fluorobenzaldehyde (3 eq., 101 mg, 0.0881 mL, 0.805 mmol) in dry DMF (2.83 mL). The mixture was heated to 130° C. for 3 days. Water and brine were added to dissolve K$_2$CO$_3$, and the mixture was extracted twice with AcOEt. The combined organic layer was dried over Na$_2$SO$_4$, filtered and concentrated to give a yellowish liquid. The analysis of the crude material showed some remaining compound 19 so the compound was re-engaged in the reaction under the same conditions. The mixture was stirred overnight and the same work-up than previously described was applied. The crude material was purified by flash chromatography (Biotage ZIP® 10 g, cyclohexane/ethyl acetate 100:0 to 70:30) to afford compound 20 (73 mg, 0.211 mmol, 79%).

[19]Fdec NMR (CDCl$_3$, 282.5 MHz): −101.8 (d, J=247 Hz, 1F); −114.2 (brd, J=247 Hz, 1F).

Synthesis of Compound 21

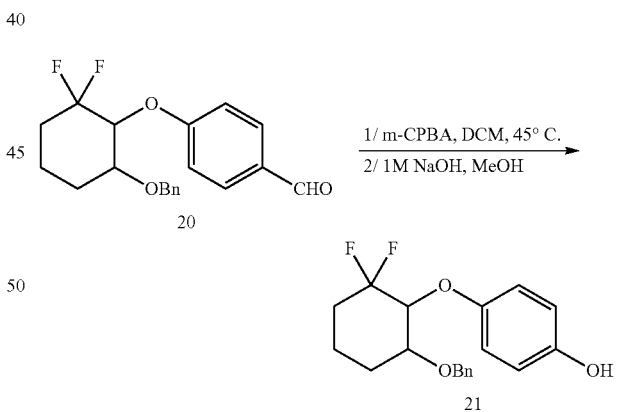

Compound 20 (1 eq., 72 mg, 0.208 mmol) was added to a solution of m-CPBA (3.5 eq., 163 mg, 0.291 mL, 0.728 mmol) in dry DCM (3.47 mL) under an inert atmosphere. The reaction mixture was stirred at 45° C. for 16 hours. The mixture was then washed with sat. NaHCO$_3$ and extracted twice with DCM. The combined organic layer was dried over Na$_2$SO$_4$, filtered and concentrated to give a yellowish residue which was dissolved in methanol (0.866 mL). NaOH 1M (5 eq., 1.04 mL, 1.04 mmol) was added and the mixture was stirred at room temperature for 1 h. The pH was adjusted to 2 with 2N HCl, and the mixture was filtered. The filtrate was extracted twice with DCM and the combined organic layer was dried over Na$_2$SO$_4$, filtered and concentrated to afford crude compound 21 (64 mg, 92%, contains mCPBA residues).

Mass (ESI$^-$): 333.1 [M−H]$^-$; 379.1 [M+HCOO]$^-$; 393.1 [M+CH$_3$COO]$^-$.

$^{19}$Fdec NMR (CDCl$_3$, 282.5 MHz): −104.2 (brd, J=242 Hz, 1F); −118.2 (brd, J=242 Hz, 1F).

Synthesis of Compound 16

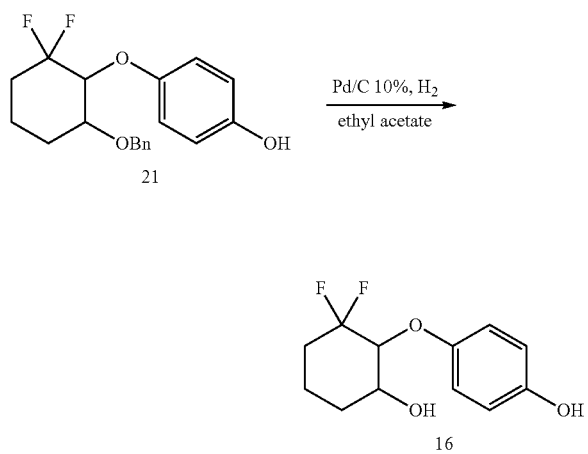

Palladium on carbon (10% w %, 0.3 eq., 60.2 mg, 0.0565 mmol) was added to a solution of compound 21 (1 eq., 63 mg, 0.188 mmol) in ethyl acetate (4 mL). The reaction mixture was stirred overnight under hydrogen pressure (10 bars). The mixture was filtered over Millipore 0.45 μm, and the black solid was washed with AcOEt. The filtrate was concentrate and purified over a flash chromatography (Biotage ZIP® 10 g, cyclohexane/ethyl acetate 85:15 to 35:65) to afford compound 16 (20 mg, 0.0819 mmol, 43%).

$^{19}$F NMR (MeOD, 282.5 MHz): −100.0 (d, J=246 Hz, 1F); −113.9 (d, J=246 Hz, 1F).

The compound 16 was obtained as a racemate mixture of the two following enantiomers 16a and 16b.

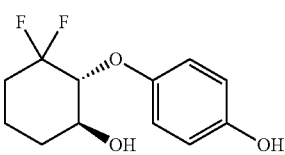

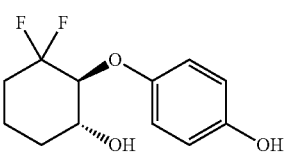

Synthesis of Compounds 22a and 22b

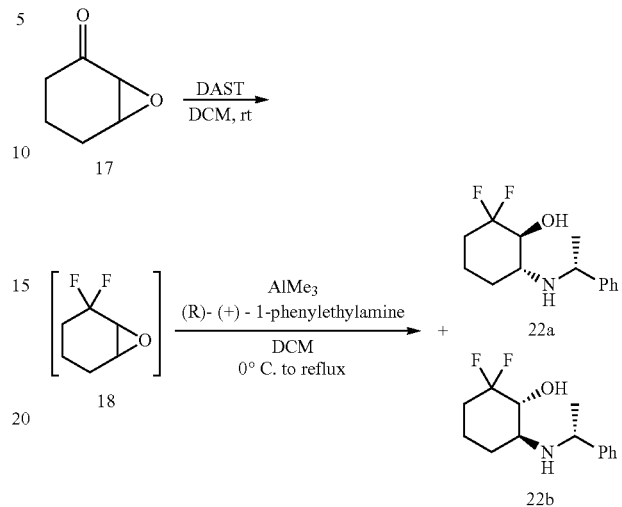

DAST (5 eq., 3.02 mL, 24.7 mmol) was added to a solution of 7-oxabicyclo[4.1.0]heptan-2-one (1 eq., 0.5 mL, 4.94 mmol) in dry DCM (5 mL) under an inert atmosphere. The reaction was stirred at room temperature for 2 h. The mixture was then slowly poured into icy water, and the layers were separated. The organic layer was filtered through a plug of silica gel (eluted with a minimum volume of DCM). The filtrate containing the difluoro epoxide 18 was cooled to 0° C. and trimethylaluminium (1.05 eq., 2 M, 2.59 mL, 5.18 mmol) was added dropwise. After stirring for 1 h, (R)-(+)-1-phenylethylamine (1.15 eq., 0.74 mL, 5.68 mmol) was slowly added, and the mixture was stirred at 0° C. for 15 min, and refluxed overnight. A saturated aqueous solution of ammonium chloride was then added to the mixture and the layers were separated. The aqueous layer was extracted with DCM, and the combined organic layer was dried over Na$_2$SO$_4$, filtered and concentrated. The crude residue was purified by a flash chromatography (Biotage®; AIT 25 g, cyclohexane/ethyl acetate 20:80 to 7:93) to afford compound 22a (420 mg, 1.65 mmol, 33%) as a yellowish solid and compound 22b (244 mg, 0.96 mmol, 19%).

Mass (ESI$^+$): 256.1 [M+H]$^+$ $^{19}$Fdec NMR (CDCl$_3$, 282.5 MHz):

22a: −103.8 (d, J=239 Hz, 1F, CF$_2$); −120.0 (d, J=240 Hz, 1F, CF$_2$).

22b: −103.8 (d, J=238 Hz, 1F, CF$_2$); −119.8 (d, J=238 Hz, 1F, CF$_2$).

Synthesis of Compounds 23a and 23b

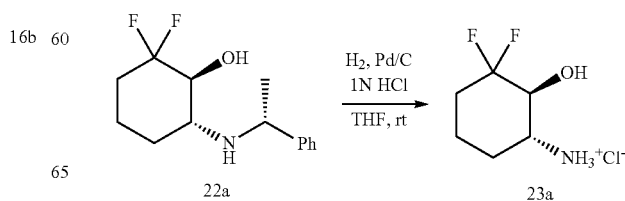

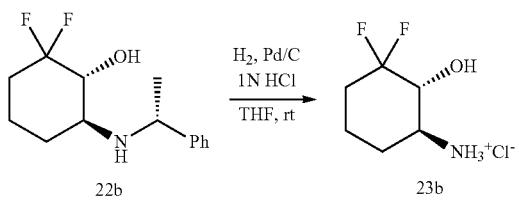

Palladium on activated carbon (0.25 eq, 20% on carbon 50% water wet 2.66 g, 4.99 mmol) and HCl 1N (1.4 eq., 1 M, 28 mL, 28 mmol) were added to a solution of 22a (1 eq., 5.1 g, 20 mmol) in THF (102 mL). The mixture was stirred overnight under hydrogen atmosphere and was then filtered over Millipore 0.45 μm. The filtrate was concentrated and co-evaporated with toluene to afford crude 23a (4.03 g, 108%) as white solid. Crude 23b (2.78 g, 104%) was obtained under the same conditions from 22b (1 eq., 3.63 g, 14.2 mmol).

Mass (ESI$^+$): 152.1 [M−HCl+H]$^+$ $^{19}$Fdec NMR (CDCl$_3$, 282.5 MHz): −106.1 (d, J=242 Hz, 1F, CF$_2$); −121.8 (d, J=242 Hz, 1F, CF$_2$).

Synthesis of Compounds 24a and 24b

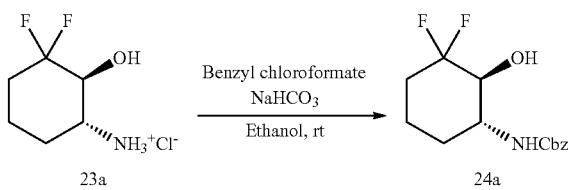

Benzyl chloroformate (1.46 eq., 4.46 mL, 31.4 mmol) and NaHCO$_3$ (3 eq., 5.41 g, 64.4 mmol) were successively added to a solution of 23a (1 eq., 4.03 g, 21.5 mmol) in ethanol (97.4 mL) under an inert atmosphere. The mixture was stirred at room temperature for 16 hours. Water was then added to the mixture, and ethanol was removed by evaporation. The aqueous solution was extracted twice with ethyl acetate, and the combined organic layer was dried over Na$_2$SO$_4$, filtered and concentrated to afford crude 24a (6.65 g, 109%) as a yellowish oil.

Crude 24b (4.74 g, 112%) was obtained under the same conditions from 23b (1 eq., 2.78 g, 14.82 mmol).

Mass (ESI$^+$): 286.1 [M+H]$^+$; 303.2 [M+NH$_4$]$^+$; 588.3 [2M+NH$_4$]$^+$.

$^{19}$Fdec NMR (CDCl$_3$, 285.5 MHz): −105.1 (d, J=243 Hz, 1F, CF$_2$); −118.2 (brd, J=243 Hz, 1F, CF$_2$).

Synthesis of Compounds 25a and 25b

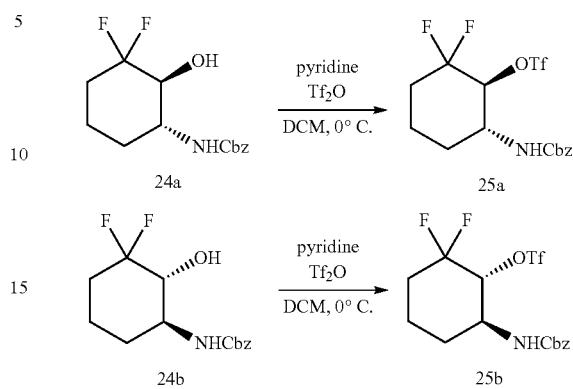

Pyridine (21.9 eq., 41.3 mL, 511 mmol) and triflic anhydride (3.27 eq., 12.7 mL, 76.3 mmol) were successively added to a solution of 24a (1 eq., 6.65 g, 23.3 mmol) in dry DCM (172 mL) cooled to 0° C., under inert atmosphere. The mixture was stirred at 0° C. for 1 hour before HCl (1.5M in water) was added. The layers were separated and the aqueous layer was extracted twice with DCM. The combined organic layer was dried over Na$_2$SO$_4$, filtered and concentrated. The crude residue was purified over a flash chromatography (Biotage®; Macherey 200 g, cyclohexane/ethyl acetate from 98:2 to 63:37) to afford 25a (4.63 g, 57% over 3 steps) in the form of a yellowish solid. 25b (4.21 g, 71% over 3 steps) was obtained under the same conditions from 24b (1 eq., 4.74 g, 16.61 mmol).

Mass (ESI$^+$): 435.1 [M+NH$_4$]$^+$ $^{19}$Fdec NMR (CDCl$_3$, 285.5 MHz): −74.5 (d, J=9 Hz, CF$_3$); −102.3 (d, J1=246 Hz, 1F, CF$_2$); −115.5 (d, J=246 Hz, 1F, CF$_2$).

Synthesis of Compounds 26a and 26b

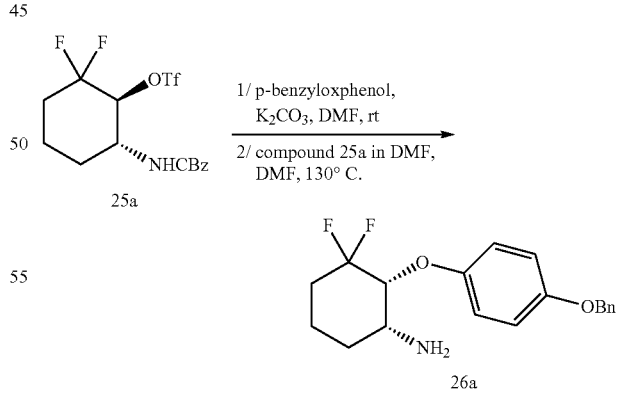

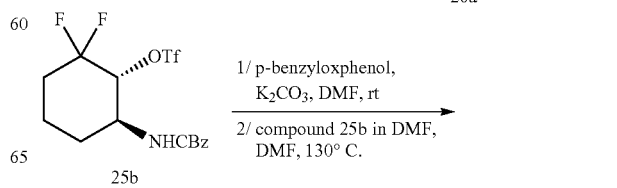

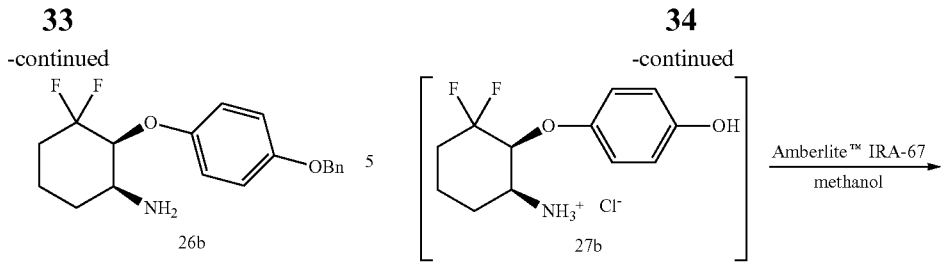

K$_2$CO$_3$ (3 eq., 4.6 g, 33.3 mmol) and benzyloxyphenol (3.5 eq., 7.77 g, 38.8 mmol) were dissolved in DMF (26.6 mL) under an inert atmosphere, and this suspension was stirred at room temperature for 1 h. A solution of 25a (1 eq., 4.63 g, 11.1 mmol) in dry DMF (10.7 mL) was then added, and the mixture was heated to 130° C. for 3 hours. Water was then added to the mixture which was extracted 3 times with ethyl acetate. The combined organic layer was washed with brine, dried over Na$_2$SO$_4$, filtered and concentrated. The resulting crude material was purified by a flash chromatography (Biotage®; SNAP 340 g, cyclohexane/ethyl acetate 97:3 to 55:45). Two purifications were required to get rid of remaining p-benzyloxyphenol. 26a (746 mg, 20%) was obtained in the form of a brown oil.

26b (1.63 g, 48%) was obtained under the same conditions from 25b (4.21 g, 10.1 mmol). Only one purification by flash chromatography was necessary.

Mass (ESI$^+$): 334.2 [M+H]$^+$ $^{19}$Fdec NMR (CDCl$_3$, 285.5 MHz): −101.1 (d, J=242 Hz, 1F, CF$_2$); −117.0 (d, J=242 Hz, 1F, CF$_2$).

Synthesis of Compounds 28a and 28b

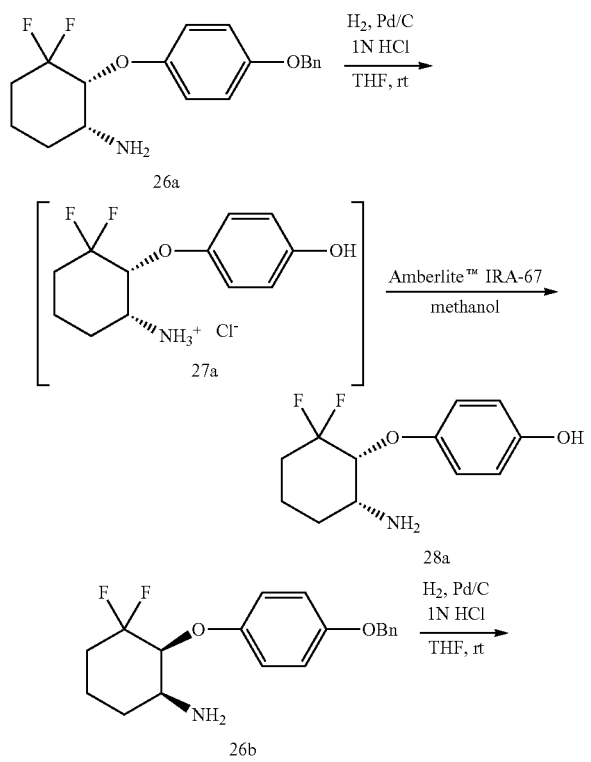

Palladium on activated carbon (0.1 eq, 20% on carbon 50% water wet, 118 mg, 0.22 mmol) and HCl 1N (1.4 eq., 1 M, 3.13 mL, 3.13 mmol) were added to a solution of 26a (1 eq., 745 mg, 2.23 mmol) in THF (65.7 mL). The mixture was stirred overnight under hydrogen atmosphere and was then filtered over Millipore 0.45 μm. The solid residue was washed with methanol and the filtrate was concentrated to afford crude 27a (743 mg, 119%) as white solid. This solid was then dissolved in methanol and Amberlite™ IRA-67 was added until pH>7. The suspension was filtered and the filtrate was concentrated to afford 28a (289 mg, 54% over 2 steps) as a white solid.

28b (140 mg, 58% over 2 steps) was obtained under the same conditions from 26b (333 mg, 1 mmol).

Mass (ESI$^+$): 244.1 [M+H]$^+$.

$^{19}$Fdec NMR (MeOD, 285.5 MHz): −101.4 (d, J=243 Hz, 1F, CF$_2$); −117.4 (brd, J=243 Hz, 1F, CF$_2$).

2. Biological Activity

In Vitro Efficacy of Compound 8 as Human Tyrosinase Inhibitor

The efficacy of compound 8 was evaluated by the inhibition of human tyrosinase in-tubo and compared to the prior art compound deoxyarbutin.

Methods

The assay was performed with a ready-to-use kit from Feldan Inc (Canada): the HumanLike Tyrosinase Assay kit (ref A021-a-001Kit).

The protocol was performed as described in the instructions for use of the manufacturer. Briefly, this kit is intended for the determination of human tyrosinase activity in presence of different inhibitors. The kit measures the conversion of L-Tyrosine into a dopachrome complex absorbing at 490 nm. The time course of the assay is 20 minutes, after which the results are analyzed and compared.

Results

The compound 8 and deoxyarbutin have been tested at a final concentration of 1.12 mM. The measured absorbances at 490 nm are reported in the table 1 and plotted in function of time in the FIG. 1.

TABLE 1 measured OD at 490 nm for 20 minutes with compound 8 and deoxyarbutin

|  |  | OD at 490 nm | | | |
|---|---|---|---|---|---|
|  |  | Deoxyarbutin 1.12 mM | Compound 8 1.12 mM | Negative control (no enzyme) | Positive control (no inhibitor) |
| time (min) | 0 | 0.0000 | 0.0000 | 0.0000 | 0.0000 |
|  | 1 | 0.0100 | 0.0080 | 0.0030 | 0.0100 |
|  | 2 | 0.0195 | 0.0170 | 0.0060 | 0.0210 |
|  | 3 | 0.0290 | 0.0245 | 0.0080 | 0.0320 |
|  | 4 | 0.0385 | 0.0345 | 0.0110 | 0.0430 |
|  | 5 | 0.0480 | 0.0415 | 0.0140 | 0.0550 |
|  | 6 | 0.0585 | 0.0505 | 0.0180 | 0.0670 |
|  | 7 | 0.0695 | 0.0610 | 0.0210 | 0.0820 |
|  | 8 | 0.0800 | 0.0675 | 0.0230 | 0.0940 |
|  | 9 | 0.0935 | 0.0755 | 0.0270 | 0.1080 |
|  | 10 | 0.1035 | 0.0845 | 0.0310 | 0.1210 |
|  | 11 | 0.1155 | 0.0935 | 0.0350 | 0.1340 |
|  | 12 | 0.1265 | 0.1015 | 0.0390 | 0.1470 |
|  | 13 | 0.1385 | 0.1090 | 0.0430 | 0.1590 |
|  | 14 | 0.1500 | 0.1165 | 0.0460 | 0.1720 |
|  | 15 | 0.1615 | 0.1255 | 0.0500 | 0.1850 |
|  | 16 | 0.1735 | 0.1355 | 0.0550 | 0.1960 |
|  | 17 | 0.1846 | 0.1405 | 0.0580 | 0.2080 |
|  | 18 | 0.1975 | 0.1495 | 0.0630 | 0.2200 |
|  | 19 | 0.2095 | 0.1575 | 0.0660 | 0.2320 |
|  | 20 | 0.2220 | 0.1665 | 0.0700 | 0.2450 |

Moreover for each compound the efficacy as tyrosinase inhibitor was calculated using the following formula:

$$\text{Inhibitor efficacy} = 100 - \left(\frac{OD_{490\,nm}\text{assay}}{OD_{490\,nm}\text{positive control (no inhibitor)}} \times 100\right)$$

The results are reported in the table 2.

TABLE 2

Inhibitor efficacy of compound 8 and deoxyarbutin at T = 20 min

|  | Inhibitor efficacy (%) |
|---|---|
| Compound 8 (1.12 mM) | 32.0 |
| Deoxyarbutin (1.12 mM) | 9.4 |

In these tested conditions, the compound 8 has shown a 3.4 times better efficacy than deoxyarbutin, on human tyrosinase inhibition in vitro.

In Vitro Effect of Compounds 8, 16 and 28a on the Inhibition of Melanin Synthesis in Human Epidermal Melanocytes Method Human melanocytes are stimulated by L-tyrosine to induce an increase of the melanin synthesis and be able to measure an inhibition of this synthesis when a whitening agent is added.

Biological model: normal human epidermal melanocytes (NHEM), lightly pigmented, were cultured in medium M254 supplemented with PMA free HMGS-2; Insulin 5 ag/ml; Penicillin 50 U/ml; Streptomycin 50 ag/ml; Gentamycin 25 µg/ml (incubator: 37° C. and 5% CO2).

Culture and treatment: melanocytes were seeded in 24-well plates and cultured in culture medium for 24 hours. The medium was then replaced by culture medium containing the test compounds or not (stimulated control) in presence of the inducer (L-tyrosine at 1 mM). The cells were then incubated for 240 hours with 2 treatment renewals after 72 and 168 hours of incubation. A non-stimulated control was performed in parallel. All experimental conditions were performed in n=3.

Melanin assay: at the end of incubation, the culture supernatants were removed and the melanin was extracted by cell lysis using a 0.5 N NaOH solution. The optical density (OD) of each experimental point was measured at 405 nm and melanin quantity was calculated using melanin standards (standard curve 0.39 to 100 µg/ml melanin). Results were expressed in g/ml of melanin.

Results

Tested Concentrations:

The compounds have been tested beforehand at different concentrations on the NHEM culture to determine the higher non-cytotoxic concentration to be used to evaluate the potential inhibition of melanin synthesis. The determined concentration was 300 µM for all compounds: 8, 16, 28a.

The results are reports in table 3.

TABLE 3

Effect of compounds 8, 16, 28a on melanin synthesis:

|  | Tested concentration | Melanin synthesis (µg/ml) | Mean (µg/ml) | Sem (µg/ml) | P[1] |
|---|---|---|---|---|---|
| Non-stimulated control | — | 7.8 | 7.6 | 0.1 | *** |
|  |  | 7.3 |  |  |  |
|  |  | 7.7 |  |  |  |
| Stimulation by L-tyrosine (1 mM) | Stimulated Control | 23.3 | 22.9 | 0.2 | — |
|  |  | 22.8 |  |  |  |
|  |  | 22.6 |  |  |  |
|  | 8 | 300 µM | 9.2 | 9.3 | 0.1 | *** |
|  |  |  | 9.4 |  |  |  |
|  |  |  | 9.2 |  |  |  |
|  | 16 | 300 µM | 7.9 | 8.1 | 0.1 | *** |
|  |  |  | 8.2 |  |  |  |
|  |  |  | 8.2 |  |  |  |

TABLE 3-continued

Effect of compounds 8, 16, 28a on melanin synthesis:

| Tested | Melanin synthesis | | Sem | |
|---|---|---|---|---|
| | concentration | (µg/ml) | Mean (µg/ml) | (µg/ml) | $P^{(1)}$ |
| 28a | 300 µM | 9.9 | 10.2 | 0.2 | *** |
| | | 10.5 | | | |
| | | 10.2 | | | |

$^{(1)}$Threshold for statistical significance
ns: >0.05, Not significant
*: 0.01 to 0.05, Significant
**: 0.001 to 0.01, Very significant
***: <0.001, Extremely significant In the tested conditions the L-tyrosine stimulation increased the synthesis of melanin up to 22.9 µg/ml (compared to 7.6 µg/ml in unstimulated control).

The tested compounds 28a, 8 and 16 have shown a high inhibition effect by decreasing the melanin synthesis to 10.2 µg/ml, 9.3 µg/ml and 8.1 µg/ml respectively.

The invention claimed is:

1. A compound having the following formula I:

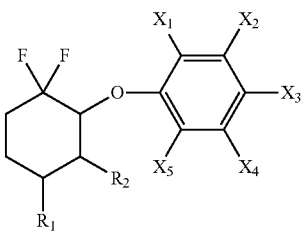

I or a cosmetically or pharmaceutically acceptable salt thereof, a stereoisomer or a mixture of stereoisomers in any proportion,
wherein:
  $R_1$ represents a hydrogen atom, OH, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$,
  $R_2$ represents OH, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, $OSO_3R_{22}$, $NH_2$, $NHR_{33}$, or $NR_{33}R_{34}$,
  $X_1$, $X_2$, $X_3$, $X_4$ and $X_5$ represent, independently from one another, a hydrogen atom, OH, $OSiR_{23}R_{24}R_{25}$, $OR_{26}$, $OC(O)R_{27}$, $OCO_2R_{28}$, $OC(O)NR_{29}R_{30}$, $OP(O)(OR_{31})_2$, or $OSO_3R_{32}$, with:
  $R_3$, $R_4$, $R_5$, $R_{13}$, $R_{14}$, $R_{15}$, $R_{23}$, $R_{24}$ and $R_{25}$ representing, independently from one another, a $(C_1-C_6)$alkyl, aryl, aryl-$(C_1-C_6)$alkyl or $(C_1-C_6)$alkyl-aryl group,
  $R_6$, $R_{16}$ and $R_{26}$ representing, independently from one another, a O-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group,
  $R_7$, $R_8$, $R_{17}$, $R_{18}$, $R_{27}$ and $R_{28}$ representing, independently from one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group,
  $R_9$, $R_{10}$, $R_{19}$, $R_{20}$, $R_{29}$ and $R_{30}$ representing, independently from one another, a hydrogen atom; a N-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group,
  $R_{11}$, $R_{12}$, $R_{21}$, $R_{22}$, $R_{31}$ and $R_{32}$ representing, independently from one another, a hydrogen atom or a $(C_1-C_6)$alkyl group, and
  $R_{33}$ and $R_{34}$ representing, independently from one another, a N-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, aryl-$(C_1-C_6)$alkyl, heteroaryl-$(C_1-C_6)$alkyl, $(C_1-C_6)$-alkylaryl or $(C_1-C_6)$-alkyl-heteroaryl group, said group being optionally substituted by one or several groups selected from a halogen atom, OH, COOH and CHO.

2. The compound according to claim 1, wherein it is a compound having the following formula Ia:

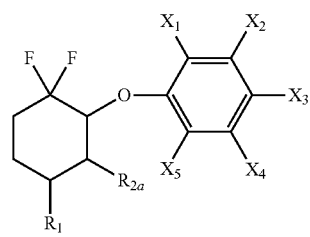

Ia or a cosmetically or pharmaceutically acceptable salt thereof, a stereoisomer or a mixture of stereoisomers in any proportion,
wherein R1, X1, X2, X3, X4 and X5 are as defined in claim 1 and R2a represents OH, OSiR13R14R15, OR16, OC(O)R17, OCO2R18, OC(O)NR19R20, OP(O)(OR21)2, or OSO3R22, with R13 to R22 as defined in claim 1.

3. The compound according to claim 1, wherein it is a compound having the following formula Ib:

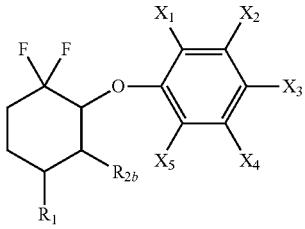

Ib or a cosmetically or pharmaceutically acceptable salt thereof, a stereoisomer or a mixture of stereoisomers in any proportion,
wherein $R_1$, $X_1$, $X_2$, $X_3$, $X_4$ and $X_5$ are as defined in claim 1 and $R_{2b}$ represents $NH_2$, $NHR_{33}$, or $NR_{33}R_{34}$, with $R_{33}$ and $R_{34}$ as defined in claim 1.

4. The compound according to claim 1, wherein R1 represents a hydrogen atom, OH, OR6, OC(O)R7, OCO2R8 or OC(O)NR9R10.

5. The compound according to claim 1, wherein $R_2$ represents $NH_2$, $NHR_{33}$, $NR_{33}R_{34}$, OH, $OR_{16}$, $OC(O)R_{17}$, $OCO_2R_{18}$ or $OC(O)NR_{19}R_{20}$.

6. The compound according to claim 1, wherein $X_1$, $X_2$, $X_3$, $X_4$ and $X_5$ represent, independently from one another, a hydrogen atom, OH, $OR_{26}$, $OC(O)R_{27}$, $OCO_2R_{28}$, or $OC(O)NR_{29}R_{30}$.

7. The compound according to claim 1, wherein at least one of $X_1$, $X_2$, $X_3$, $X_4$ and $X_5$ represents a group other than a hydrogen atom.

8. The compound according to claim 7, wherein $X_3$ represents a group other than a hydrogen atom.

9. The compound according to claim 8, wherein $X_1$, $X_2$, $X_4$ and $X_5$ each represent a hydrogen atom and $X_3$ represents a group other than a hydrogen atom.

10. The compound according to claim 9, wherein:
$X_1$, $X_2$, $X_4$ and $X_5$ each represent a hydrogen atom,
$X_3$ represents OH or $OR_{26}$,
$R_1$ represents H, OH or $OR_6$, and
$R_2$ represents $NH_2$, $NHR_{33}$, $NR_{33}R_{34}$, OH or $OR_{16}$.

11. The compound according to claim 1, wherein:
$R_6$, $R_7$, $R_8$, $R_{16}$, $R_{17}$, $R_{18}$, $R_{26}$, $R_{27}$, $R_{28}$, $R_{33}$ and $R_{34}$ represent, independently from one another, a ($C_1$-$C_6$) alkyl, aryl or aryl-($C_1$-$C_6$)alkyl group, and
$R_9$, $R_{10}$, $R_{19}$, $R_{20}$, $R_{29}$ and $R_{30}$ represent, independently from one another, a hydrogen atom, or a ($C_1$-$C_6$)alkyl, aryl or aryl-($C_1$-$C_6$)alkyl group.

12. The compound according to claim 1, wherein it is chosen among:

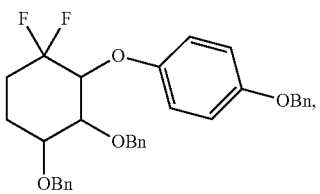

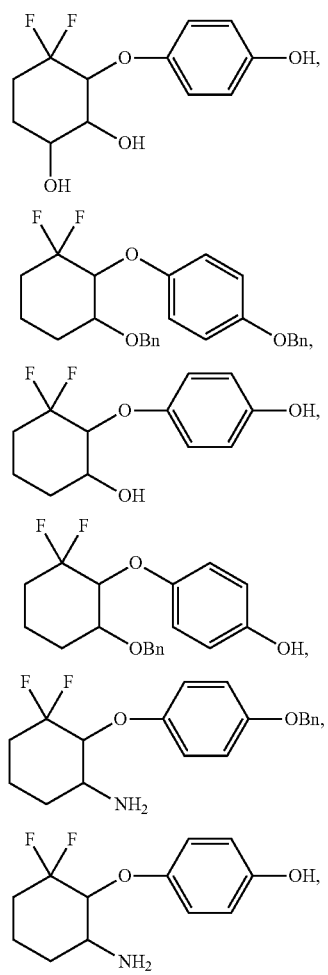

and cosmetically or pharmaceutically acceptable salts thereof.

13. The compound according to claim 12, wherein it is chosen among:

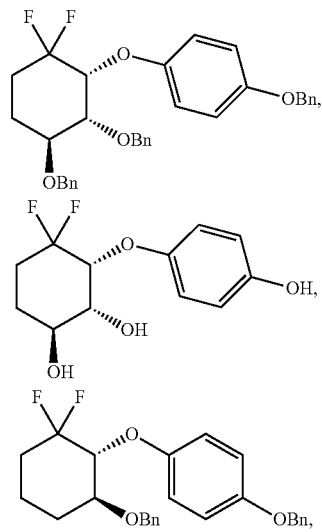

-continued

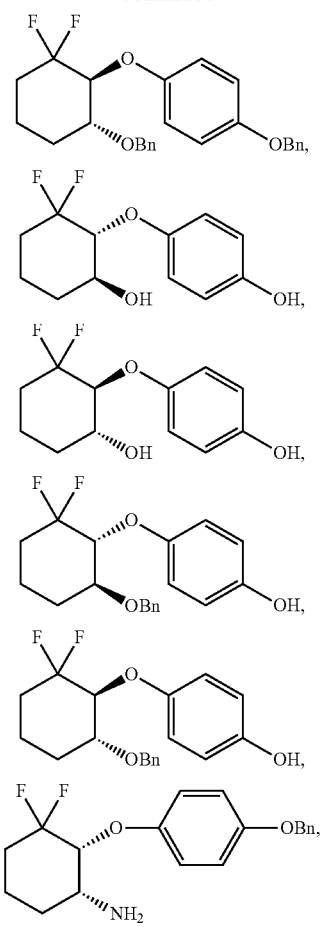

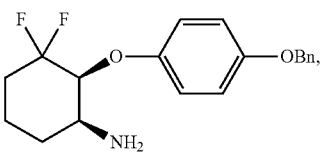

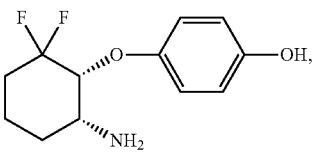

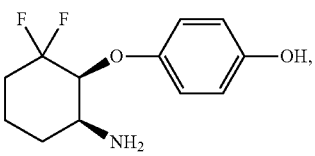

and cosmetically or pharmaceutically acceptable salts thereof.

14. A cosmetic or pharmaceutical composition comprising at least one compound according to claim 1 and at least one cosmetically or pharmaceutically acceptable excipient.

15. A method for the preparation of a compound according to claim 1 comprising:

reacting a compound of following formula II:

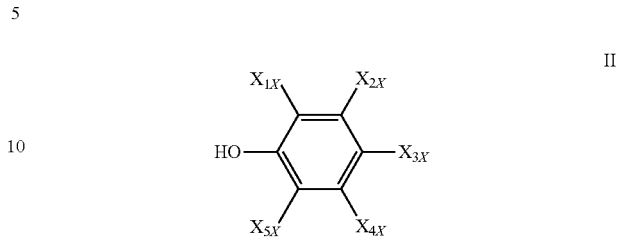

with a compound of following formula III:

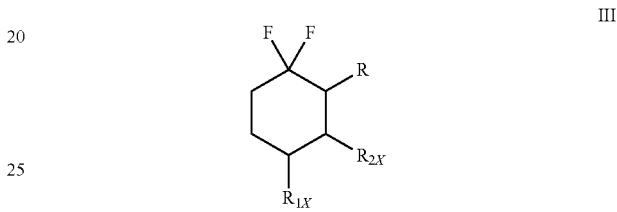

wherein $X_{1X}$, $X_{2X}$, $X_{3X}$, $X_{4X}$, $X_{5X}$, $R_{1X}$ and $R_{2X}$ represent respectively $X_1$, $X_2$, $X_3$, $X_4$, $X_5$, $R_1$ and $R_2$ as defined in claim 1, optionally in a protected form, and R represents a leaving group, deprotecting the $R_1$, $R_2$, $X_1$, $X_2$, $X_3$, $X_4$ and/or $X_5$ groups when they are in a protected form, and optionally salifying the compound of formula I obtained in the previous step to give a cosmetically or pharmaceutically acceptable salt of the compound of formula I.

16. A method for the preparation of a compound according to claim 1 comprising:

fluorinating the ketone function of a compound of following formula XI:

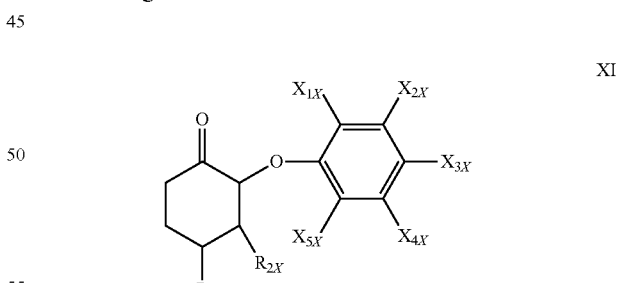

wherein $X_{1x}$, $X_{2x}$, $X_{3x}$, $X_{4x}$, $X_{5x}$, $R_{1x}$ and $R_{2x}$ represent respectively $X_1$, $X_2$, $X_3$, $X_4$, $X_5$, $R_1$ and $R_2$ as defined in claim 1, optionally in a protected form, deprotecting the $R_1$, $R_2$, $X_1$, $X_2$, $X_3$, $X_4$ and/or $X_5$ groups when they are in a protected form, and optionally salifying the compound of formula I obtained in the previous step to give a cosmetically or pharmaceutically acceptable salt of the compound of formula I.

17. A method for the preparation of a compound according to claim 1 with $X_3$=OH comprising:

oxidizing the aldehyde function of a compound of following formula XV:

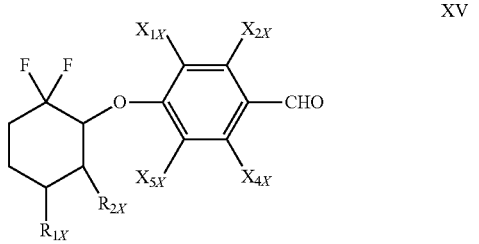

XV wherein $X_{1X}$, $X_{2X}$, $X_{4X}$, $X_{5X}$, $R_{1X}$ and $R_{2X}$ represent respectively $X_1$, $X_2$, $X_4$, $X_5$, $R_1$ and $R_2$ as defined in claim 1, optionally in a protected form, deprotecting the $R_1$, $R_2$, $X_1$, $X_2$, $X_4$ and/or $X_5$ groups when they are in a protected form, and optionally salifying the compound of formula I obtained in the previous step to give a cosmetically or pharmaceutically acceptable salt of the compound of formula I.

18. The method according to claim 17, wherein the compound of formula XV is prepared by reacting a compound of following formula XVI:

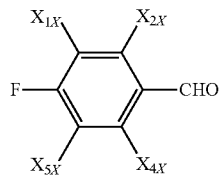

wherein $X_{1X}$, $X_{2X}$, $X_{4X}$ and $X_{5X}$ are as defined in claim 17, with a compound of following formula XIV:

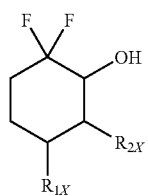

XIV wherein $R_{1X}$ and $R_{2X}$ are as defined in claim 17.

19. A method for depigmenting, lightening, bleaching or whitening a skin by applying on said skin an efficient amount of a compound according to claim 1 to a person in need thereof.

20. A method for treating a pigmentation disorder of a skin by applying on said skin an efficient amount of a compound according to claim 1 to a person in need thereof.

21. The method according to claim 20, wherein the pigmentation disorder is a hyperpigmentation.

22. The method according to claim 21, wherein the hyperpigmentation results from overexposure to the sun, inflammation, injuries, burns, medicines or hormonal alteration.

* * * * *